(12) United States Patent
Pasieka

(10) Patent No.: US 6,587,945 B1
(45) Date of Patent: Jul. 1, 2003

(54) TRANSMITTING REVIEWS WITH DIGITAL SIGNATURES

(75) Inventor: Michael S. Pasieka, Thornwood, NY (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/221,955

(22) Filed: Dec. 28, 1998

(51) Int. Cl.[7] .............................. H04L 9/32; G06F 17/60
(52) U.S. Cl. ................................... 713/176; 705/3
(58) Field of Search ......................... 713/176, 177, 713/178, 179, 168; 705/3, 67, 75

(56) References Cited

U.S. PATENT DOCUMENTS 5,606,609 A    2/1997  Houser et al. ............... 380/4
5,659,616 A *  8/1997  Sudia .......................... 380/30
6,188,766 B1 * 2/2001  Kocher ........................ 358/405

* cited by examiner

Primary Examiner—Matthew Smithers
(74) Attorney, Agent, or Firm—Michael E. Belk

(57) ABSTRACT

A document is created and digitally signed using an author's private key. The signed document is provided to an electronic notary who notarizes (provides a time/date stamp and signs the time/date stamp using the notary's private key) the authors signed document. A reviewer requests and verifies the origin and integrity of the authors signed document using the author's public key. As the reviewer examines the documentary, a log is automatically created. The review log and reviewed document are digitally signed using the reviewer's private key and the signed reviewed document is provided to an electronic notary who notarizes the signed reviewed document. An auditor requests the reviewed document. The auditor verifies the origin and integrity of the document using the notary's public key. The auditor audits the signed review document.

26 Claims, 21 Drawing Sheets

TRANSMITTING REVIEWS WITH DIGITAL SIGNATURES

FIELD OF THE INVENTION

The invention is related to the field of cryptography and more specifically to cryptographically timestamping documents to prove their existence at a certain time.

BACKGROUND OF THE INVENTION

In many common situations, people need to verify that a digital document (i.e. a document such as a contract or receipt that is digitally stored in a computer system) existed on a certain date. That is, we may need to prove that no one has altered or revised the digital document since a certain date such as the alleged creation date or distribution date of the document.

One method of providing such proof is known as electronic notarizing or timestamping. A one-way hash of the document is produced, and the hash is encrypted using a private key of the owner of the document in order to form a so called digital signature. The document signature is sent to a digital notary or time stamper who combines the digital signature with a digital stamping time (digital representation of the time and date) to form a time stamp, and the notary hashes the time stamp and encrypts the time stamp hash using the digital notary's private key to form another digital signature called the time stamp signature. Then the notary sends a record including the time stamp and the time stamp signature to the author. Anyone with access to the time stamp and notary's signature can then hash the time stamp and use the notary's public key to decrypt the notary's signature and compare the hash to the decryption to prove that the author's signature, and thus the document, existed when the time stamp was created, and that, the author's signature and the stamping time were originally encrypted together by someone who had access to the notary's private key.

Notarizing digital documents is disclosed in U.S. Pat. No. 5,136,646. Notarizing by secure hardware in a system is disclosed in U.S. Pat. No. 5,001,752. Public key cryptography is disclosed in "New Directions in Cryptography" by Diffie and Hellman in IEEE Transactions On Information Theory, Vol IT-22, November 1976, pp 644–654 and in U.S. Pat. No. 4,405,829 to Rivest and U.S. Pat. No. 4,868,877. One-way hashing is disclosed in "Collision-Free Hash Functions and Public Key Signature Schemes", Advances in Cryptology-Eurocrypt '87, Springer-Verlag, LNCS, 1988, vol. 304, pp. 203–217.

The above citations are hereby incorporated in whole by reference.

SUMMARY OF THE INVENTION

It is an object of the invention to provide methods and apparatus for the authentication of review activity logs of digital documents.

In the inventions disclosed herein, a first document is reviewed and a digital log (review document) of review activities during a review of the first document and then the review document is digitally signed and the signature is notarized in such a way, that the relationship between the first document and the review document can be proved as well as the origination and integrity of the review document and the time of the review document's notarization.

It is another object of the invention to provide methods and apparatus for authenticating presentations that document critical procedures.

In the invention a digital activity log of a critical procedure is produced and the activity log is digitally signed and notarized, so that, the integrity and origination of the activity log can be proved.

In one embodiment of the invention, an image is created and sent to a secure server. The server signs the image (hashes the image and encrypts the hash) and sends the server's image signature to an electronic notary which notarizes the image signature. Preferably, the notary returns a time stamp and time stamp signature for the image signature (image time stamp and notary's image signature) to the server. Then upon request, the server sends the image and server's image signature to a reviewer who uses the signature to verify the origin and integrity of the image. The reviewer may also receive the image time stamp and notary's image signature and verify the time of notarization of the image. Then the reviewer (human) reviews the image and the reviewer's workstation automatically creates a review activity log (review) which is returned to the server. The server combines the review with information indicating that the review is related to the image. The identifying information may be, for example, the image hash, image signature, image time stamp or notary's image signature. Then, the server signs the combination and sends the server's review signature to the notary which notarizes the server's review signature.

Preferably, the notary returns a review time stamp and notary's review signature to the server. Then upon request, the server sends the image, image signature, review, and review signature to an auditor who can verify the origin and integrity of the review, that the review was based on the image, and the origin and integrity of the image. The server may also send the image time stamp, notary's image signature, review time stamp, and notary's review signature to the auditor who can verify the time of notarization for the image and review. Then the auditor can review the quality of the image and the quality of the review.

In another embodiment of the invention, a report is signed by the author before the report is sent to the server. Then the report and author's signature are sent to a server which sends the author's signature to the notary which notarizes the author's signature. Preferably, the notary returns a time stamp and time stamp signature for the report to the server. Then, later upon request, the server sends the report and report signature to the reviewer who can use the report signature to verify the origin and integrity of the report. The server may also send the report time stamp and notary's signature to the reviewer who can verify the time at which the report was notarized. The human reviewer reviews the report and the reviewer's workstation automatically creates a review (log of activities and conclusions of the review process). Then, information indicating the relationship between the review and the original document is combined with the review and the combination is signed by the reviewer. The review and reviewer's signature are sent to the server which sends the reviewer's signature to the notary which notarizes the reviewer's signature. Preferably, the notary returns a review time stamp and a notary's review signature to the server.

In a third embodiment of the invention, a multimedia presentation is produced in order to document the activities performed during a critical procedure, so that, the correctness of the procedure can be demonstrated. The author signs the presentation and sends the presentation signature to an electronic notary who notarizes the signature. Preferably, the electronic notary creates a time stamp for the presentation, signs the time stamp, and returns the presentation time stamp and notary's presentation signature to the author. Then upon request, the author sends the presentation, the presentation time stamp, and the notary's presentation signature to the reviewer. The reviewer verifies the origin and integrity of the presentation and verifies the time of notarization in the presentation time stamp. As the human reviewer reviews the presentation, the reviewer's workstation automatically creates a review (review activities log). When the review is complete the reviewer signs the review and sends the reviewer's signature to an electronic notary. The notary creates a time stamp, signs the time stamp, and returns the time stamp and notary's signature for the review to the reviewer. Then upon request, the reviewer sends the review and review signature as well as the time stamp and notary's signature for the review to an auditor. The auditor verifies the origin and integrity of the review and verifies the time of notarization. Also, the notary requests the presentation and presentation signature from the author as well as the time stamp and notary's signature for the presentation. The auditor verifies the origin and integrity of the presentation and verifies the time of the notarization. Then the auditor reviews the quality of the presentation and/or the quality of the review.

As described above, in embodiments where the notary returns a time stamp and time stamp signature, they can be distributed to allow others to verify the time of notarizing of the digital documents. Alternatively, or in addition, other methods of verifying the time of notarization can be provided. Time stamps can be authenticated by having the notary resign the time stamp and return the signature and then checking whether the old and new signatures match. Another method of authenticating time stamps, is to provide information from the time stamp or the notary's signature to the notary and requesting that the notary use the information to find the notary's record of the time stamp and signature, and return information regarding success or failure or return the time stamp and signature, from the notary's records. Another method of authenticating time stamps, is for the notary to always return one or more previous and subsequent time stamps to the customer, and then the customer can contact other customers identified in the subsequent time stamps and request those customers to verify the time for the time stamp.

Other alternatives and advantages of applicant's inventions will be disclosed or become obvious to those skilled in the art by studying the detailed description below with reference to the following drawings which illustrate the elements of the appended claims of the inventions.

DETAILED DESCRIPTION OF THE PREFERRED EMBODIMENT

Figure 1A:
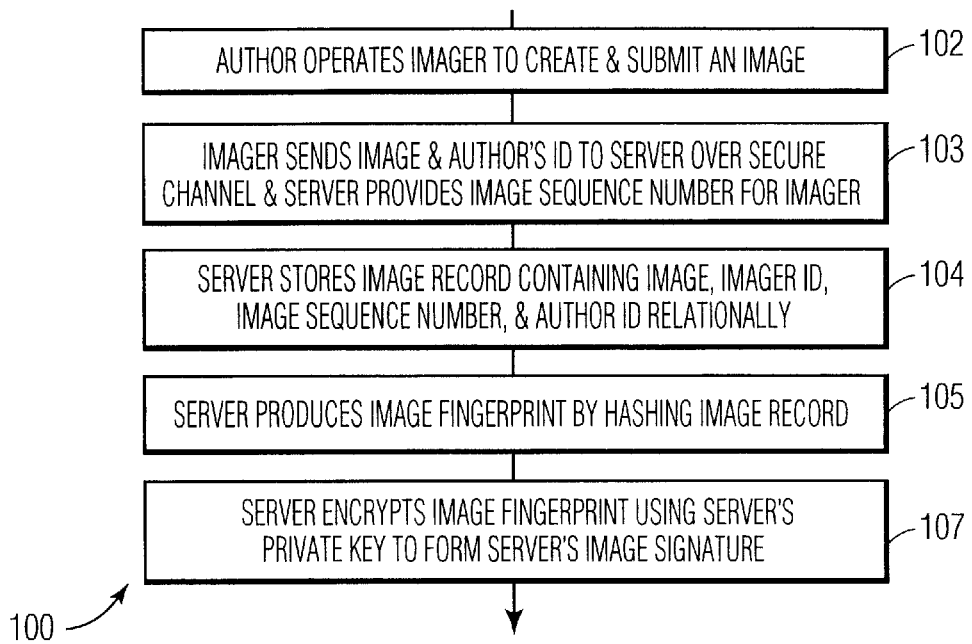
FIGS. 1a–1h shows a flow chart of a first specific embodiment of the invention for authenticating image reviews.

FIGS. 1a–1h show a first specific embodiment of the invention for authenticating reviews. In a first group of steps 100 in FIG. 1a, an author uses an imager to create an image and the image is automatically sent to a server which signs and stores the image. In step 102, the author operates an imager to create an image and initiates submitting the image to a secure server. The imager may include any equipment that produces an image such as a text page scanner, digital still camera, fax machine, medical scanner (electrocardiogram/angiogram, ultrasound imager, computerized axial tomograph, magnetic resonance imager, X-ray machine) or any other method of making images. Also, the images may be video images and/or audio images such as a cardiac sound recording or a medical record dictation. In step 103, the imager transmits the image to a secure server over a secure channel. The secure channel may be an encrypted message over a public network or an non-encrypted message over a private (secure) network with sufficient security precautions, depending on the nature of the information. Preferably, the transmission will identify the author and the imager device. The server may return an image sequence number for the imager to facilitate later access to the image. In step 104, the server combines the imager ID (or author ID) and image sequence number with the image to produce an image record and stores the image record. Preferably, the items of information in the image record are stored relationally so they can easily be retrieved based on, for example, a keyword search. Herein, relationally just means that, the fact that some information item is related to another information item and vice versa is also stored in the workstation. In this case the items of the image record are stored relationally with each other. In step 105, the server hashes the image record using a one-way hash to produce an image fingerprint. The advantage of a one-way hash is that it can not be reversed to decrypt the report, so that, even if the report were confidential or private the fingerprint would not have to be kept confidential. A hash of a digital document is commonly referred to as a digital fingerprint. In step 107, the server encrypts the image fingerprint using the server's private key (or author's or imager's private keys stored in the server) to form an image signature. The purpose of the encryption is to provide proof that the author is the originator of the image, and that the image has not been altered by others since it was signed. The encryption of the hash has nothing to do with keeping the data or the hash secret but only to prove integrity and origin of the image.

The server has a private key that can be used to encrypt digital information and which is kept confidential from other parties. The other parties have a related public key that can be used to decrypt information that was encrypted using the private key. That is, the server has made the public key publicly available, for example, by posting the public key on another non-secure server or by publishing the key. Others who which to verify the origin of the image (e.g. that the imager connected to the server produced the image) or integrity of the image (i.e. that the image has not been changed or replaced with another image since it was signed by the server), can use the image record, image signature and the public key for such verification.

The author ID (or scanner ID) and image sequence number are included in the image record to provide evidence of the origin of the image. Where such evidence is not required they may be omitted. Other information such as the digital image creation time (date and time) can be included. It is possible to only hash together selected parts of the image record to produce the image fingerprint, if desired. Alternately, the imager or author could have different unique private/public password (key) pairs assigned to them that could be used to prove the origination of the image so the imager ID or author ID would not have to be combined with the image before hashing. The server would have access to the private keys for signing the images and provide others with the public keys.

Figure 1B:
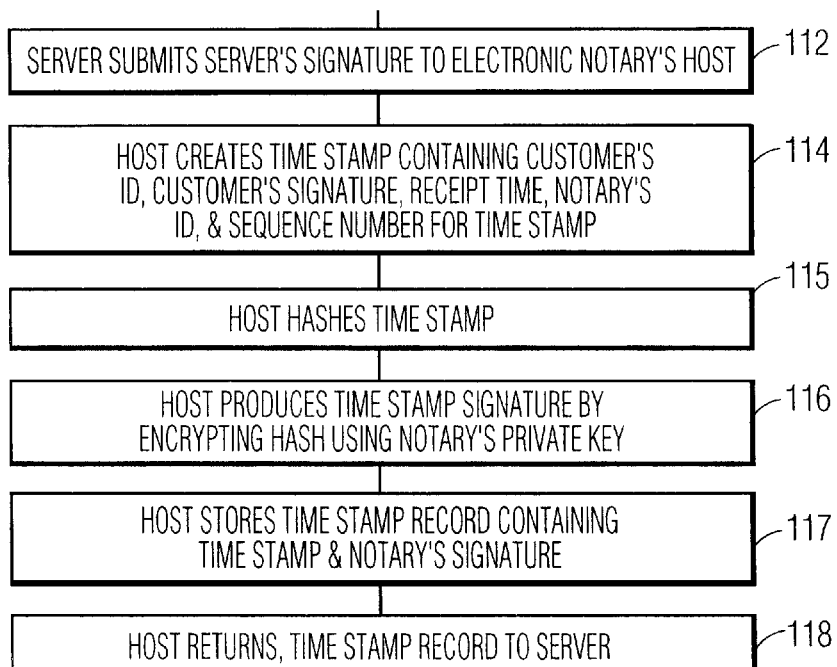

In the next group of steps 110, in FIG. 1b, the server obtains a time stamp and a time stamp signature from an electronic notary for the server's image signature. In step 112, the server establishes a connection with the notary's host network, and the server sends the server's image signature to the host. The channel does not need to be secure since the image signature is not confidential. In step 114, the host creates an image time stamp containing the server's image signature and the digital time of the time stamping (e.g. receipt time or stamping time). Preferably the notary ID, the sequence number of the time stamp (this is different than the sequence number of the image), and the server ID are also included in the time stamp. In step 115, the host hashes the image time stamp, to produce a time stamp fingerprint, and in step 116, the host signs the time stamp hash (fingerprint) using the notary's private key to produce a time stamp signature for the image. In step 117, the host produces a time stamp record for the image containing the image time stamp and the notary's image signature and stores the information items of the record relationally in the notary's protected storage. In step 118, the host transmits the image time stamp record back to the server.

Figure 1C:
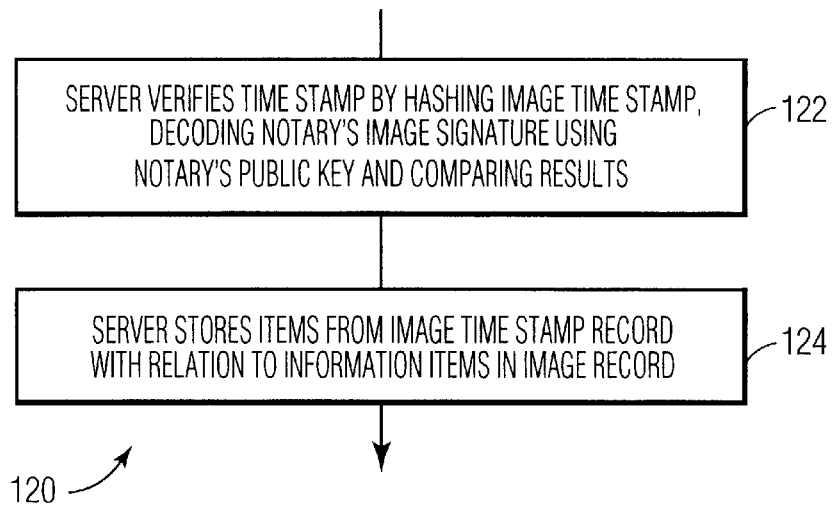

In the next group of steps 120, in FIG. 1c, the server verifies and stores the time stamp record. In step 122, the server hashes the image time stamp and decrypts the notary's image signature using the notary's public key in order to verify the integrity and origin of the image time stamp and the notary's image signature. If they match, the server knows that the signature and time stamp are from the notary (or at least someone with access to the notary's private key) because it was the notary's public key that decrypted the signature, and the server also knows that the signature and time stamp have not been altered since the notary signed the time stamp. In step 124, the server stores the information items of the notary's image time stamp record with relation to the information items in the image record and the server's image signature.

Figure 1D:
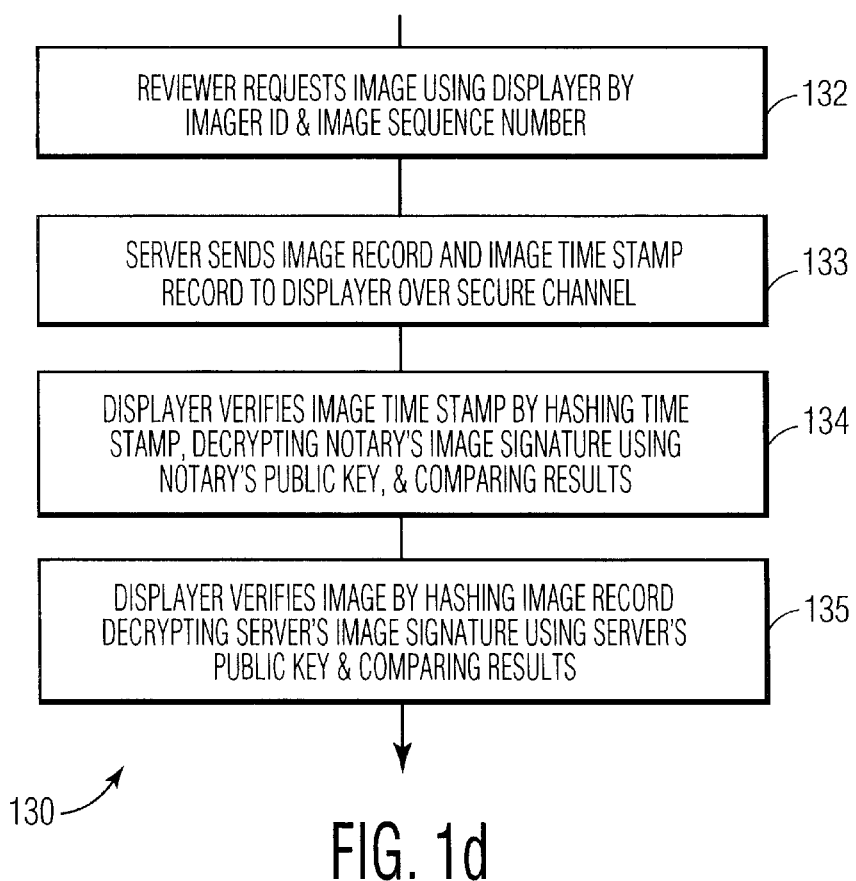

In the next set of steps 130, in FIG. 1d, a reviewer (human user) requests the image for reviewing the image using a displayer and the stored image record is provided by the server along with and the image time stamp record, and the displayer verifies the origin, integrity, and time of notarization of the image. In step 132, the reviewer requests the image using the displayer, for example, by specifying an imager ID and image sequence number. The displayer may be any equipment that allows the image to be played to the user. The displayer is not restricted to visual display and may be, for example, a loud speaker playing an audio image. In step 133, the server sends the image record and the time stamp record for the image to the displayer over a secure channel (if the image is confidential). In step 134, the displayer hashes the image time stamp and decrypts the notary's image signature using the notary's public key in order to verify the digital time of notarization and other information in the image time stamp. In step 135, the displayer produces the image fingerprint and decrypts the servers's image signature (from the image time stamp) using the server's public key and compares the decryption with the fingerprint to verify the origin and integrity of the image. If they match, the reviewer knows that the signature and report are from the server (or at least someone with access to the server's private key) because it was the server's public key that decrypted the signature, and the reviewer also knows that the signature and report have not been altered since the author signed the report.

Figure 1E:
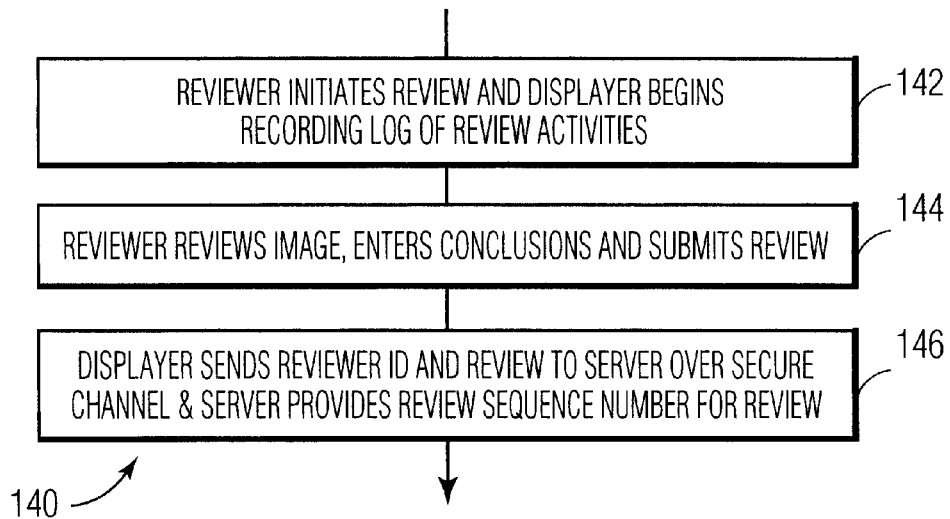

In the next few steps 140, in FIG. 1e, of this embodiment of the invention, the reviewer reviews the image as the displayer automatically generates a log of the review activities (review), the reviewer enters his conclusions and submits the review, and then the displayer sends the review back to the server. In step 142, the reviewer initiates recording of a review activities log (review) for the image by, for example, entering a command into a user interface of the displayer to display the image. In the review the displayer may record the begin time and end time during which the reviewer displays the image. Alternately, the review may contain the total time during which the image was displayed. The review may also include any keystrokes or audio dictation the reviewer enters to record comments or conclusions about the image. The workstation documents the configuration of the workstation including the revision level of all the software on the workstation and the hardware connected to the workstation. If portions of the image are subject to manipulations, such as zooming, changing contrast, changing color assignments, and various digital image enhancements, they are logged in the review. The reviewer may be able to look at multiple windows on a display or on multiple displays, for example, to compare two images or the same image with different image enhancements. In this case, the review may contain a log indicating which windows or displays the reviewer looks at in what order and for how long. Preferably, the activities log would include a video showing what the reviewer is examining. Preferably, enough information would be gathered, so that, the log could be played to show the views that the reviewer looked at in the same order for the same time. If the image is a product of a compressed transmission (e.g. MPEG II), it may be possible to request at least portions of the raw uncompressed image for improving enhancements of interesting portions of the image, and such access would be included in the log. Such a system would especially be useful for critical activities such as medical image reviews. Alternately, other known methods could be used to determine what monitors the reviewer is studying during the review.

In step 144, the reviewer enters conclusions and submits the review activities log. For example, in a simple system, the reviewer may press a button on the displayer indicating that there is nothing interesting on the image and the image would be replaced by the next image, and the review log would contain the amount of time that image was viewed and the fact that the results were negative. On the other hand, in a more elaborate system, the review log may include a video of the reviewer's activities during the review with extensive audio comments about whatever is shown on the image. Of course conclusions may be entered through every part of a more extensive review, but typically comments will be entered at least at the end of the review.

In step 146, the displayer sends the review and review record's ID to the server over a secure channel and server returns a sequence number for the review. The displayer forms a review record that includes the review and preferably, other information, such as, the reviewer's ID, a review title, and the displayer ID, and sends it to the server over a secure channel. The server returns a receipt and may return a sequence number or other ID, so that, the reviewer can be easily accessed.

Figure 1F:
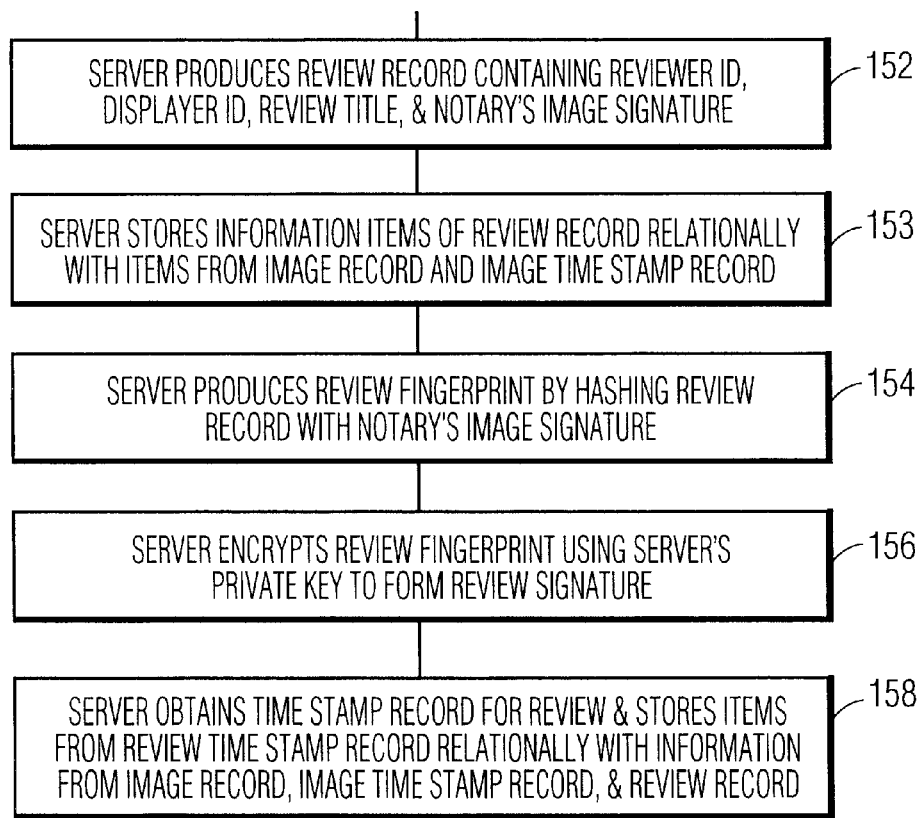

In the group of steps 150, in FIG. 1*f*, for this embodiment of the invention, the server stores the review record, verifies the review record, and obtains a time stamp record for the review. In step 152, the server produces a review record containing the information received from the displayer possibly along with other information such as a receipt time, displayer ID, and review sequence number. In step 153, the items of information in the review record are stored relationally with the items of information in the image record and image time stamp record. In step 154, the server produces a fingerprint of the review record by combining the imager ID and image sequence number with the review record and hashing the combination. Combining the imager ID and image sequence number with the review record provides evidence that the review is based on the image. Alternately, other items that can be used to uniquely identify the image, could be combined with the review such as an image hash, the server's image signature, the image time stamp, the combination of the notary's ID and time stamp sequence number, or the notary's image signature.

In step 156, the server produces a review signature by encrypting the review fingerprint using the server's private key. Finally, in step 158, the server obtains a time stamp record for the review. This step incorporates all of steps 112–124 shown in FIGS. 1*b* and 1*c*, except in this case, those steps are performed for the review rather than for the image. The description of those steps above is sufficient for those skilled in the art to understand step 158.

Figure 1G:
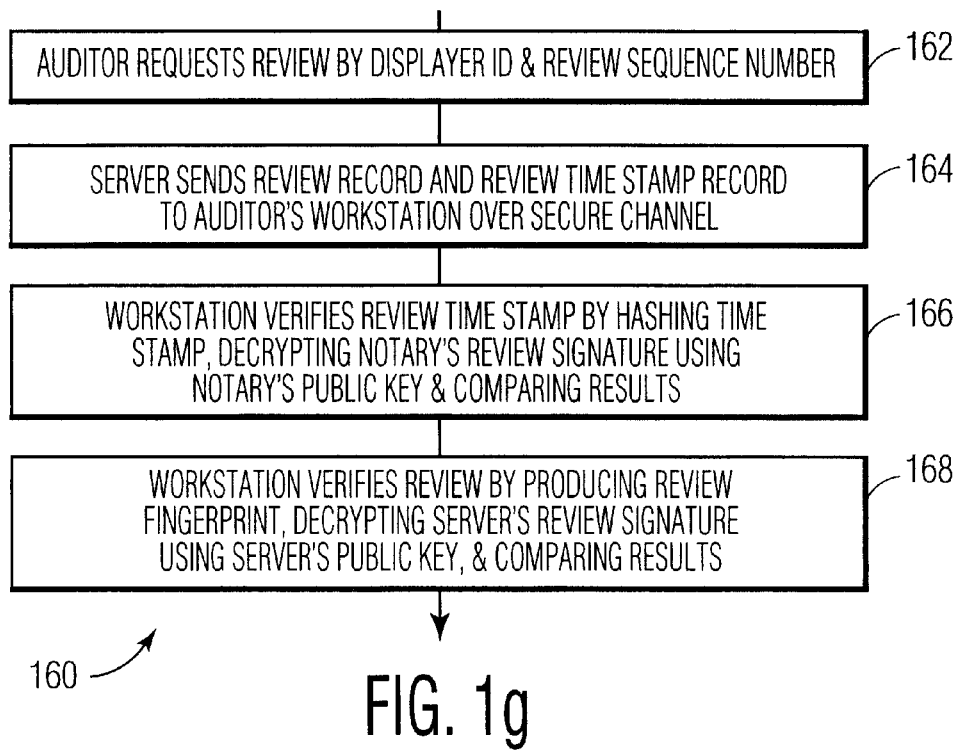

In the next set of steps 160, in FIG. 1*g*, an auditor (human user) requests the review record and review time stamp record and verifies the review time stamp and review. In step 162, the auditor requests the review record and review time stamp from the server using an auditing workstation by, for example, specifying the displayer ID and review sequence number. The auditor's workstation may be any equipment that allows the review to be played based on the image, so that, the auditor can determine the quality of the image and the quality of the review. In step 164, the server sends the review record and the review time stamp record to the auditor's workstation. In step 166, the workstation hashes the review time stamp and decrypts the notary's review signature using the notary's public key, and compares the decryption to the hash in order to verify the digital time of notarization and other information in the image time stamp. In step 168, the workstation verifies the review by producing the review fingerprint and decrypting the server's review signature (from the review time stamp) and compares the decryption with the fingerprint in order to verify the origin and integrity of the review.

Figure 1H:
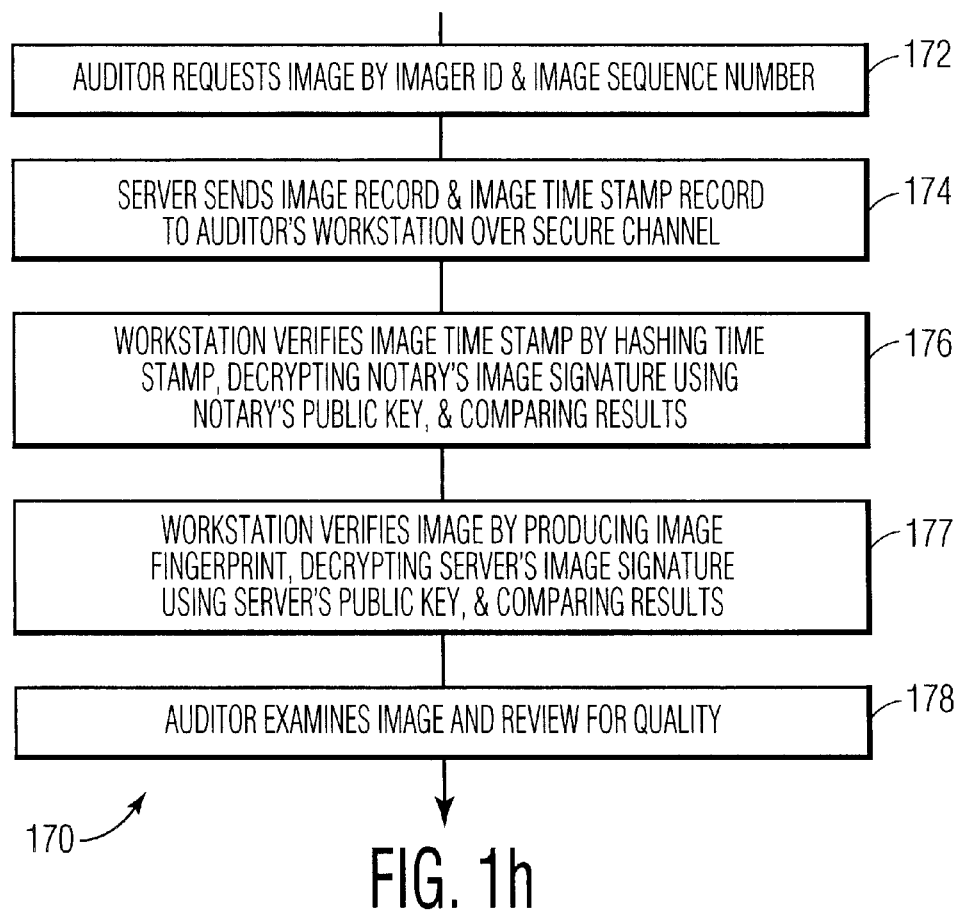

In the final group of steps 170, in FIG. 1*h*, the auditor requests the image record and image time stamp record and verifies the image and image time stamp and then audits the image and review for quality. In step 172, the auditor requests the image from the server by specifying, for example, the imager ID and image sequence number, and in step 174, the server sends the image record and the time stamp record to the workstation. In step 176, the workstation verifies the image time stamp by hashing the image time stamp and decrypting the notary's image signature using the notary's public key, and comparing the hash to the decryption. In step 177, the workstation produces the image fingerprint and decrypts the servers's image signature (from the image time stamp) and compares the decryption with the fingerprint to verify the origin and integrity of the image. Finally, in step 178, the auditor plays the review based on the image, so that, the auditor can determine the quality of the image and the quality of the review of the image.

Figure 2A:
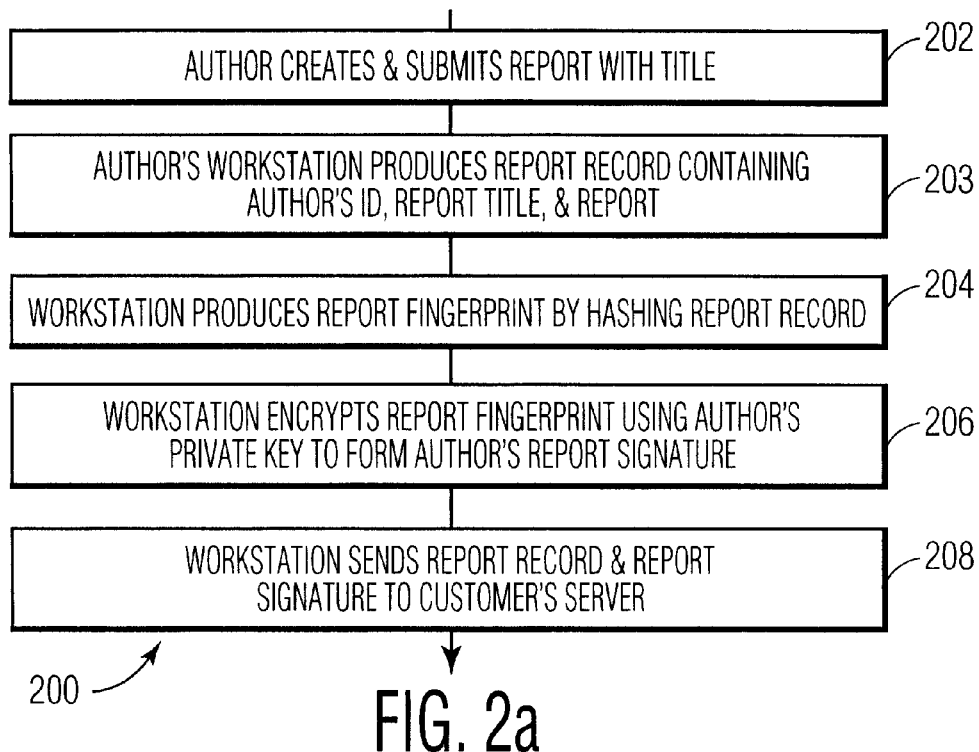
FIGS. 2a–2i shows another flow chart for a second specific embodiment of the invention for authenticating report reviews.

FIGS. 2*a*–2*i* show a second specific embodiment of the invention for authenticating reviews. FIG. 2*a* illustrates a first group of steps 200 of the method of the invention, in which software loaded in the author's workstation is used for creating and signing a digital document, so that, others can authenticate the origin and integrity of the document and for storing the document and signature.

In step 202, an author creates a report (digital document) using software loaded onto the workstation which is connected to a server in a network, and the author inputs a command to submit the report to the server. The report may include any digital information such as written text, filled out forms, scanned images, and sound recordings.

The report contains the type of information that someone may desire to prove originated from the author and has not been altered. For example, the report may be a medical report, a contract or other legal papers, a safety or specification compliance report of a building under construction, or any other collection of information that needs to be protected from unauthorized alteration or replacement.

In step 203, the author's workstation produces and stores a report record containing the report. Preferably, the report record also contains the author's ID and the report title. Other information may also be included in the report record such as the editing history for creating the report, the creation time of the report, the workstation ID. Preferably, the items of information in the report record are stored relationally so they can easily be retrieved based on, for example, a keyword search. In this case, relationally just means that, the fact that the report is related to the hash and signature and vice versa is also stored in the workstation. In step 204, the author's workstation preferably hashes the report record using a specified one-way hashing method to form a report fingerprint. In step 206, the workstation encrypts the report fingerprint using the author's private key (or private key of the workstation) to form the author's signature for the report. The author has a private key that can be used to encrypt digital information and other parties have a public key that can be used to decrypt the information.

Preferably, the workstation stores the author's signature in the storage of the workstation relationally with the items of information in the report record. In order to save space, after the workstation receives a receipt from the server indicating that the report record and author's signature are safely stored, then the workstation may delete those items, or archive them onto removable media or otherwise remove the information from the random access storage of the workstation. In step 208, the workstation sends (transmits) the report record and the author's signature for the report to a customer's server. If the contents of the report are confidential or private then a secure channel is established between the workstation and the server before the transmission and the server is a secure server. A secure channel may be a transmission of encrypted data through a public network or of non-encrypted data through a private (secure) network with reasonable security precautions taken depending on the confidentiality of the information.

Figure 2B:
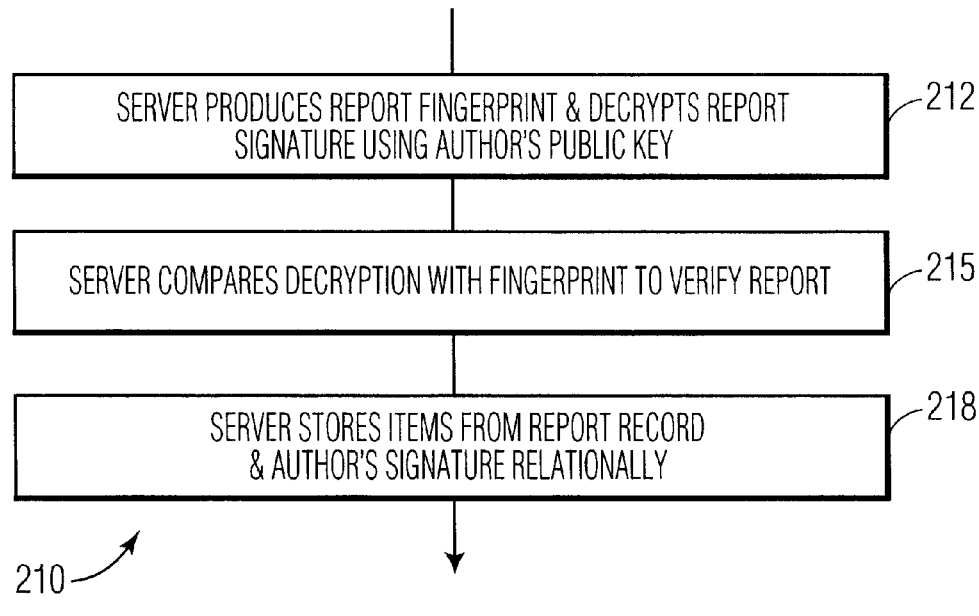

In the second group of steps 210, of the second embodiment of the invention, in FIG. 2b, the server verifies and stores the report. In step 212, in order to authenticate the report, the server hashes the report record to produce the same report fingerprint as described above in step 204. Also, the server decrypts the author's signature using the author's public key. Then in step 215, the server compares the report fingerprint to the decrypted signature to verify that they match. If they match, the server knows that the signature and report are from the author (or at least someone with access to the author's private key) because it was the author's public key that decrypted the signature, and the server also knows that the signature and report have not been altered since the author signed the report. In step 218, the server stores the report record. Preferably, the items of the report record and the author's signature are stored relationally in the server's secure storage, so that, they can be easily accessed. When the report record and author's signature are safely stored then the secure server may send a receipt to the workstation, so that, the workstation removes at least the report from active storage.

Figure 2C:
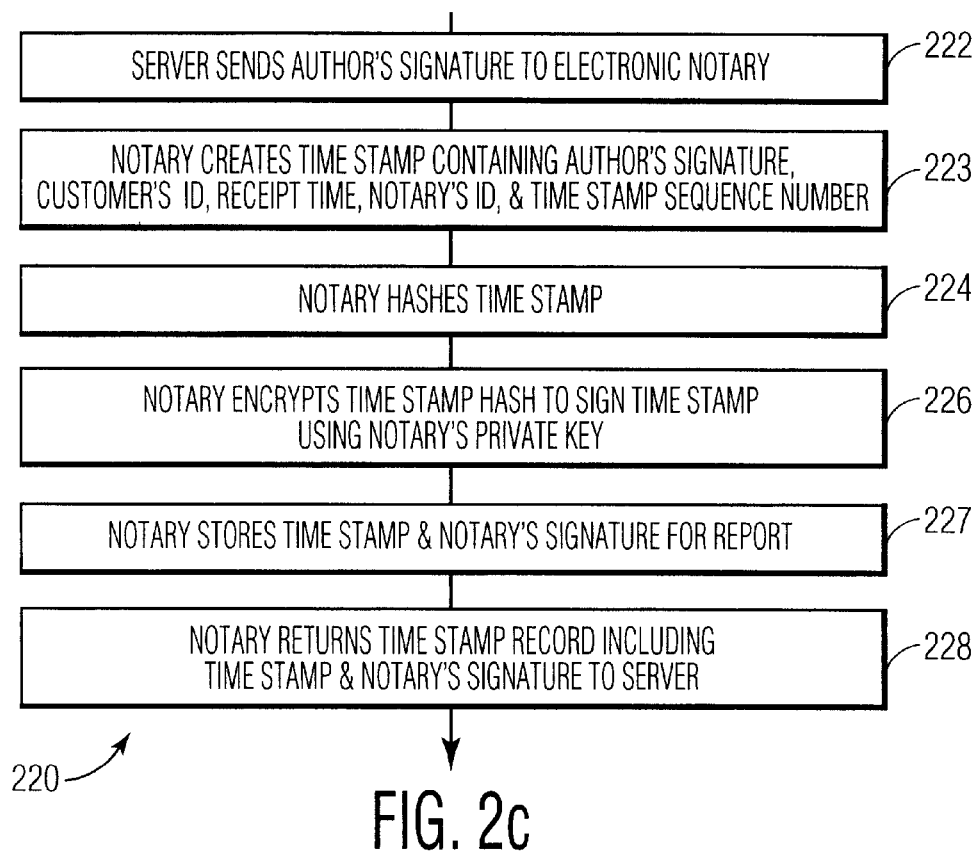

In a next group of steps 220, in FIG. 2c, the server obtains a time stamp and time stamp signature for the author's report signature, from an electronic notary. In step 222, the server sends the author's report signature to a notary's host system over the network. Since the signature is not confidential, high security is not required for signature transmission, so that, a secure channel is not required. Alternately, the notary could be a secure part of the hardware of the server, for example, a device with a private key that the owner of the server would not know or be able to discover without destroying the device. In step 223, the host creates a time stamp containing the author's signature and the receipt time (or time of creating the time stamp). Preferably, the notary ID, time stamp sequence number, and customer ID are also included in the time stamp. The customer ID may be associated with the server or with some or all of the servers of a customer. In step 224, the notary hashes the time stamp and in step 226, the notary signs the time stamp hash by encrypting the time stamp using the notary's private key.

The notary publicly provides a public key which can be used to decrypt the notary's signature. Anyone with access to the time stamp and notary's signature, can hash the time stamp and decrypt the notary's signature using the public key and compare the hash to the decrypted signature and determine if they match. If they match it proves that the signature was produced by the notary and that the information in the time stamp has not been changed since it was signed by the notary. Since the time stamp includes a stamping time and the author's report signature it proves that the signature existed at the time of stamping and that the report existed at some time before the stamping.

In step 227, the electronic notary stores the time stamp and the notary's signature for the report relationally, for example, on a secure disk drive system of the notary. In step 228, the notary transmits to the server, a time stamp record for the report, including the report time stamp and the notary's report signature for the time stamp. Also, one or more previous and subsequent time stamp records may be sent in a package to the customer's server, so that, by contacting the customers identified in the subsequent time stamp records, the authenticity of the time stamp can be verified independently from the notary.

Figure 2D:
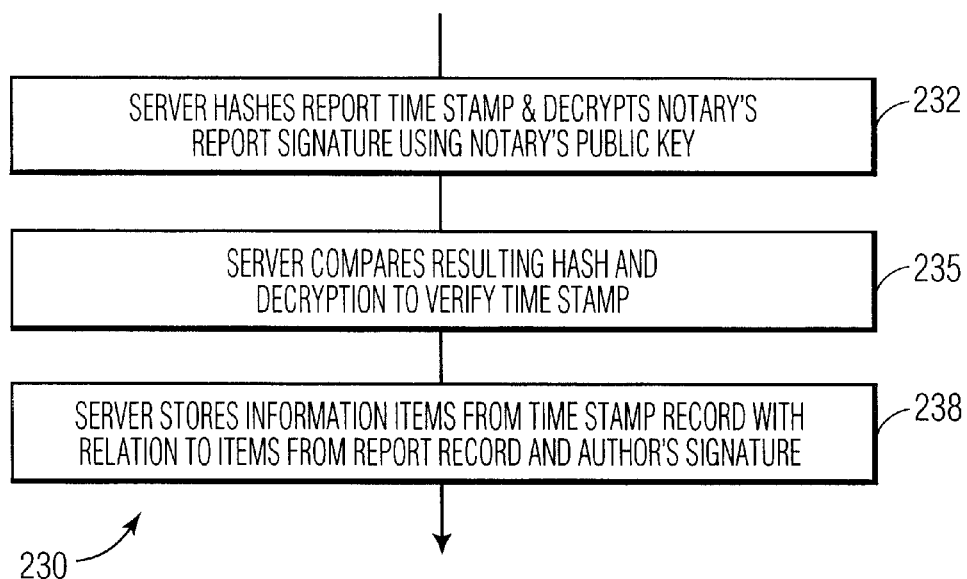

In the next group of steps 230, in FIG. 2d, the server authenticates and stores the time stamp record. In step 232, in order to authenticate the report time stamp, the server hashes the time stamp and decrypts the notary's report signature using the notary's public key. In step 235, the server compares the time stamp hash with the decrypted time stamp signature, and if there is a match, then the time stamp is authenticated. That is, the server knows that the time stamp and notary's signature are from the notary and have not been altered since the time stamp was signed. In step 238, the server stores the information items from the time stamp record (and any previous and subsequent time stamp records) with relation to the information items in the report record.

Figure 2E:
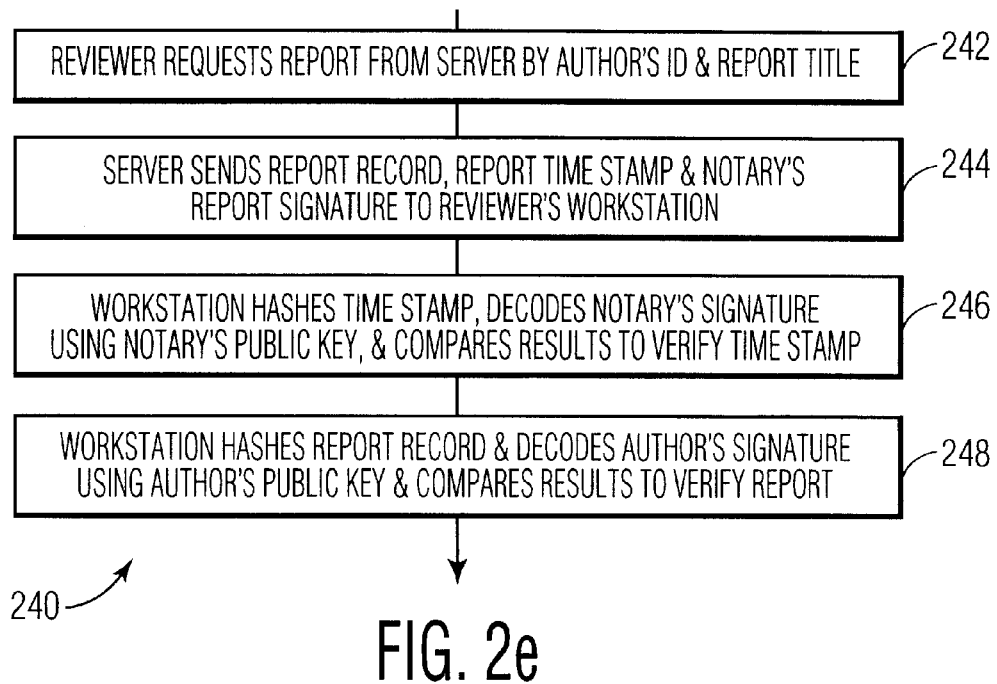

In the next group of steps 240, in FIG. 2e, a reviewer (human user) obtains a copy of the report (first document) and verifies its origin and integrity. In step 242, the reviewer uses a review workstation (displayer) to request the report from the server by specifying, for example, the author's ID and report title. The reviewer could be using the same workstation as was used by the author or a different workstation. In step 244, the server sends the report record and report time stamp record to the reviewer's workstation through a secure channel. In step 246, the reviewer's workstation hashes the time stamp and decrypts the notary's signature using the notary's public key to verify the time stamp. That is, if the hash and the decryption of the signature match then the workstation knows that the notary's signature was produced from the time stamp by someone with access to the notary's private key and thus, that the information in the time stamp existed when the signature was produced. Since the time stamp contains the author's signature for the report and the time (including date) at which the notary's signature was produced, it proves that the author's signature existed at that time and the report existed at some previous time. In step 248, the workstation hashes the report and decrypts the author's signature (contained in the time stamp) using the author's public key, and compares the results to verify the author's signature. That is, if the hash and the decryption of the author's signature match then the report was signed by someone with access to the author's private key and the report has not been changed since it was signed.

Figure 2F:
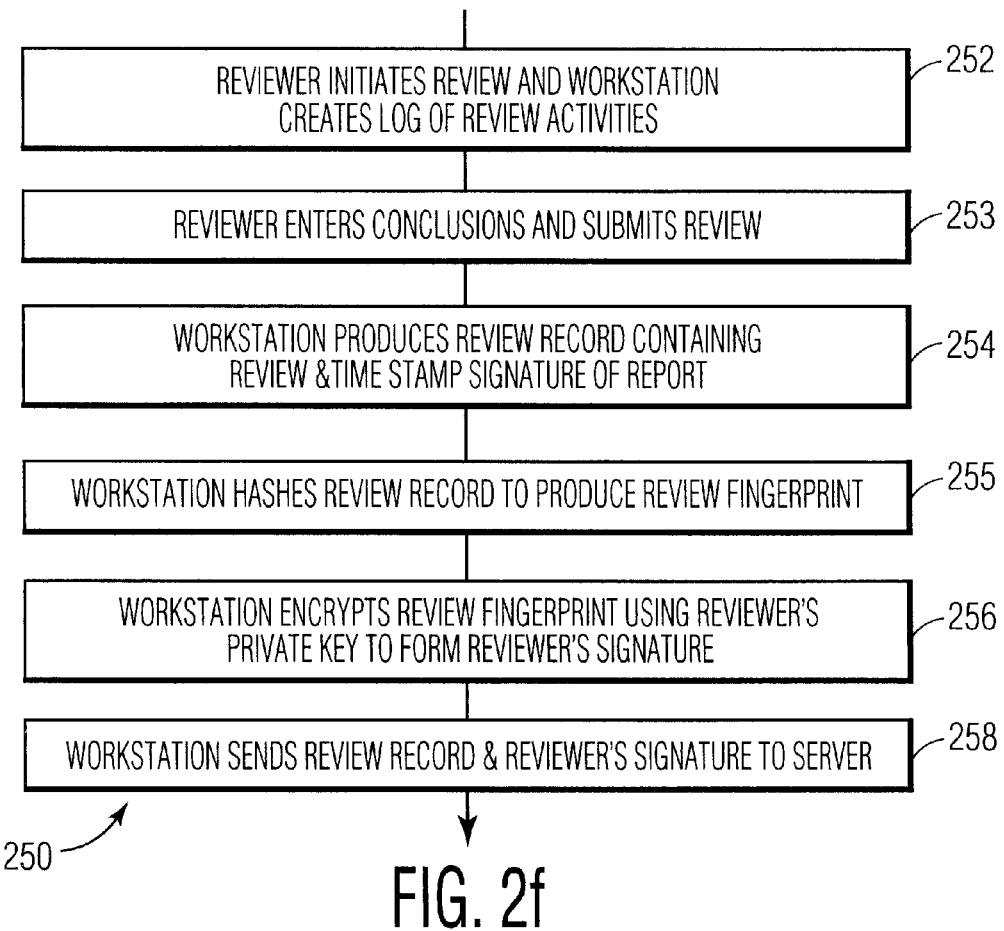

In the next group of steps 250, in FIG. 2f, of this second embodiment, the reviewer reviews the report as a log is produced to document the review activity and the resulting review activity log (review) is digitally signed. In step 252, the reviewer initiates the review of the report by, for example, specifying the author ID and report title and the workstation automatically records the review activities in the log. In the log, the workstation documents the configuration of the workstation including the revision level of all the software on the workstation and the hardware connected to the workstation. Then, as the reviewer reviews the report, the workstation documents every step of the review including which parts of the report are examined, and how long and in what order they are examined. If portions of the report are subjected to manipulations such as zooming, slow motion, contrast adjustment, changes in color, or other digital image enhancements, then those manipulations are recorded in the log. The reviewer may dictate or otherwise enter review information and conclusions into the review (log) during the review. Preferably, the workstation includes one or more video cameras and microphones and a video and audio record of the reviewer's activities are made to document the actual extent of the review, that is, what the reviewer was looking at, his expression, his comments during the review. Preferably, the recording of the log is performed in the background, so that, it does not interfere with the review process, but the reviewer is expected to enter comments about the report during the review and preferably conclusions at the end of the review.

In step 253, the reviewer enters conclusions of the review of the report into the review activity log (review) and inputs a command to submit the review to the server. In step 254, the workstation combines the review log and the report time stamp to form a review record. Other information may also be included in the review record, such as, the reviewer's ID, the workstation ID, the review title, a review sequence number for the workstation. In step 256, the workstation hashes the review record to produce a review fingerprint. The purpose for combining the time stamp with the review log before signing is to document that the review is a review of the report.

Alternatively, or in addition to the time stamp, other information proving that the review is for the report could be combined with the review log before hashing, such as, the author's report signature, the report fingerprint, the combination of the author's ID and the report title, or the time stamp signature for the report. In step 256, the workstation encrypts the review fingerprint using the reviewer's (or workstation's) private key to form the reviewer's signature. The workstation may store the review, and the reviewer's signature, if desired. In step 258, the workstation sends the review record, and reviewer's signature to the server. In order to save space the review can be deleted or achieved from the reviewer's workstation as soon as the server returns a receipt for the review.

Figure 2G:
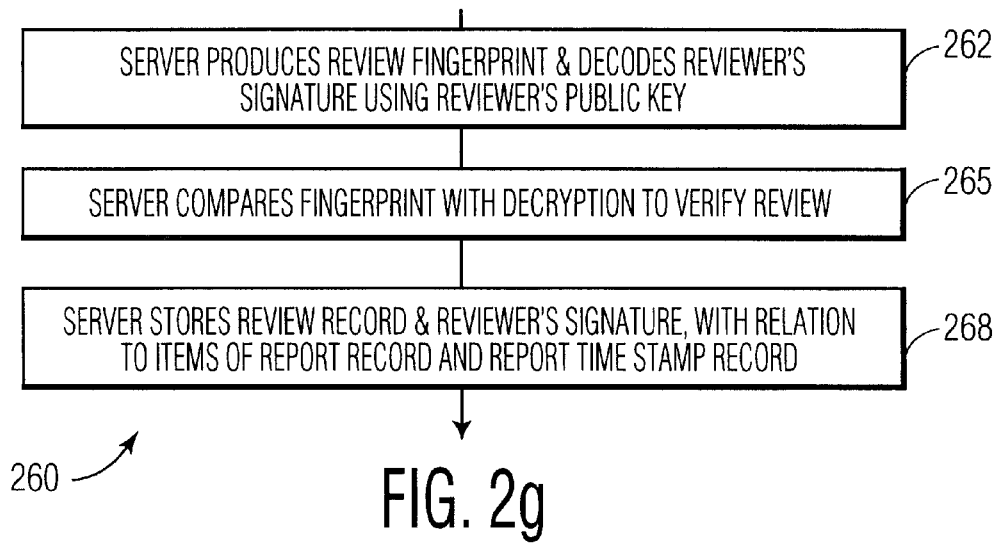

In another group of steps 260, in FIG. 2g, of this first specific embodiment, the server authenticates the review record an stores the review record and reviewer's signature. The server can then return a receipt to the review workstation, so that, the review can be deleted to same storage space on the review work station. In step 262, the server hashes the review record to form a review fingerprint, and decrypts the reviewer's signature using the reviewer's public key. In step 265, the server compares the decrypted signature with the fingerprint to verify the origin and integrity of the review. If the results match then the server knows that the review is from the reviewer, the review is based on the report, and the review and signature have not been changed since the reviewer signed the review. In step 268, the secure server stores the review record and the reviewer's signature with relation to the information related to the report.

Figure 2H:
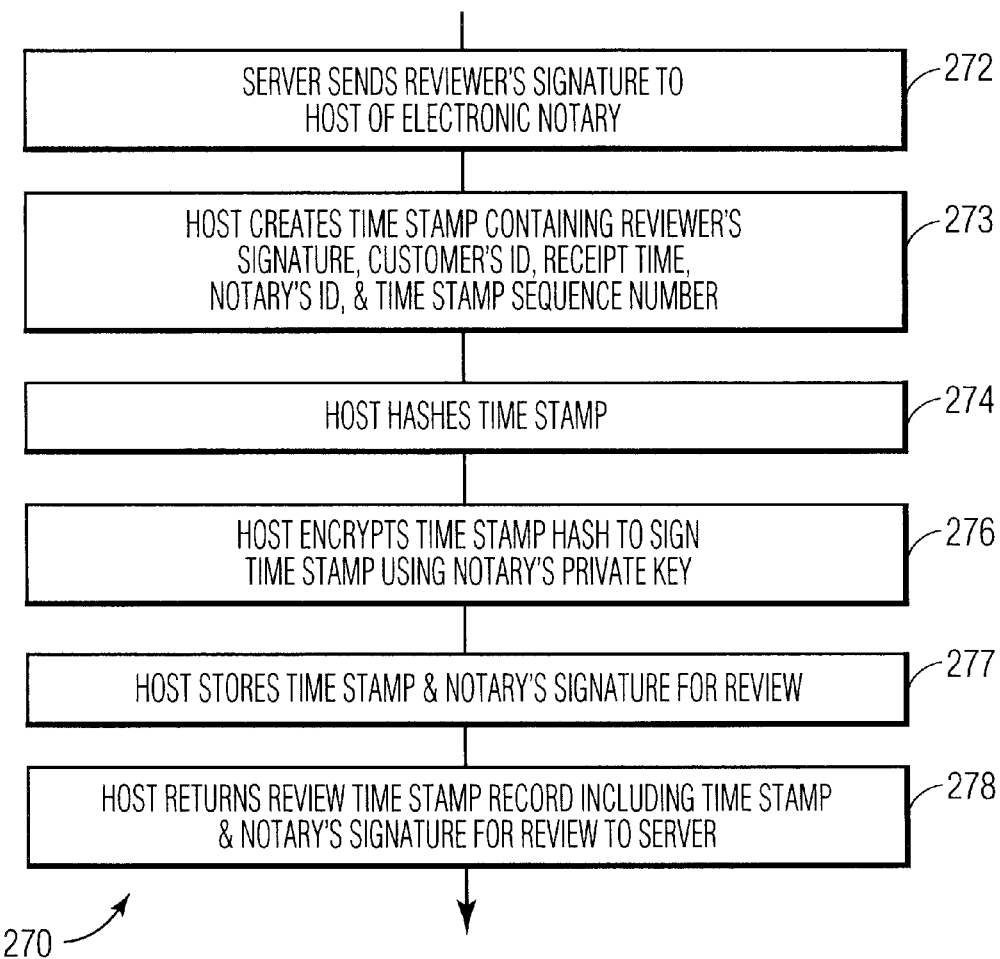

In the next group of steps 270, in FIG. 2h, of the second specific embodiment of the invention, the server sends the reviewer's signature to an electronic notary which produces a time stamp, signs the time stamp, stores the time stamp and its signature, and returns the time stamp and signature to the server. These steps are similar to the steps 220, in FIG. 2c, which should be referred to, and only the differences will be discussed below. In step 272, the server sends the reviewer's signature to the electronic notary. In step 273, the notary's host creates a time stamp that contains the reviewer's signature and the receipt time. Preferably, the notary's ID, a time stamp sequence number, and the customer ID for the server are also included in the time stamp. In step 274, the host hashes the time stamp, and in step 276, the host encrypts the time stamp hash to sign the time stamp using the notary's private key. In step 277, the host stores the time stamp and notary's signature, and in step 278, the notary's host returns a review time stamp record including the review time stamp and the notary's review signature to the server.

Figure 2I:
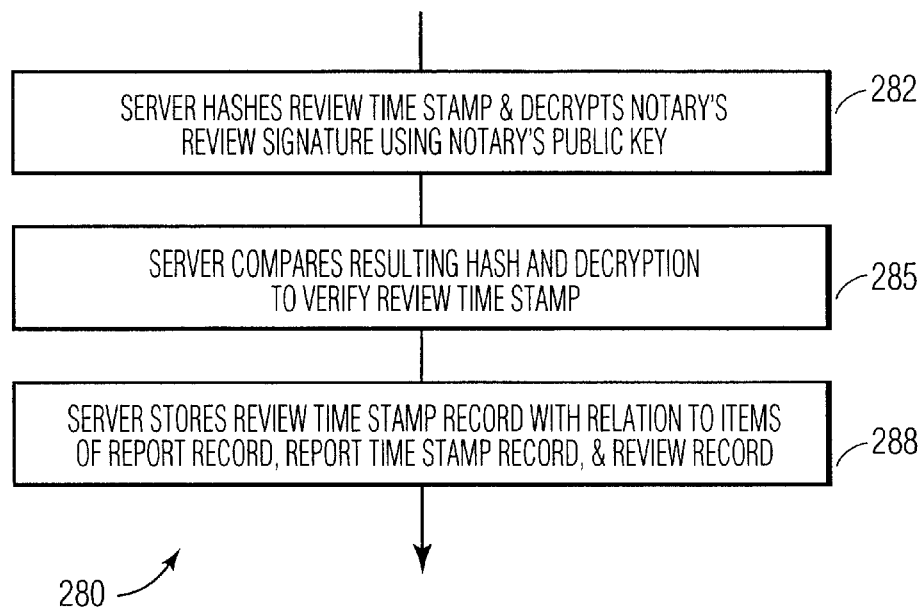

In the final group of steps 280, in FIG. 2i, for this embodiment, the server verifies the notary's time stamp and time stamp signature for the review, and stores the review time stamp record. These steps are similar to steps 230 in FIG. 2d, discussed above, which should be referred to for details, so only the differences will be discussed below. In step 285, the server hashes the review time stamp and decrypts the notary's review signature. In step 288, the server compares the hash and decryption to verify the review time stamp and notary's review signature. In step 284, the server stores the review time stamp and notary's review signature with relation to the information items in the report record, report time stamp record, and review record.

Figure 3A:
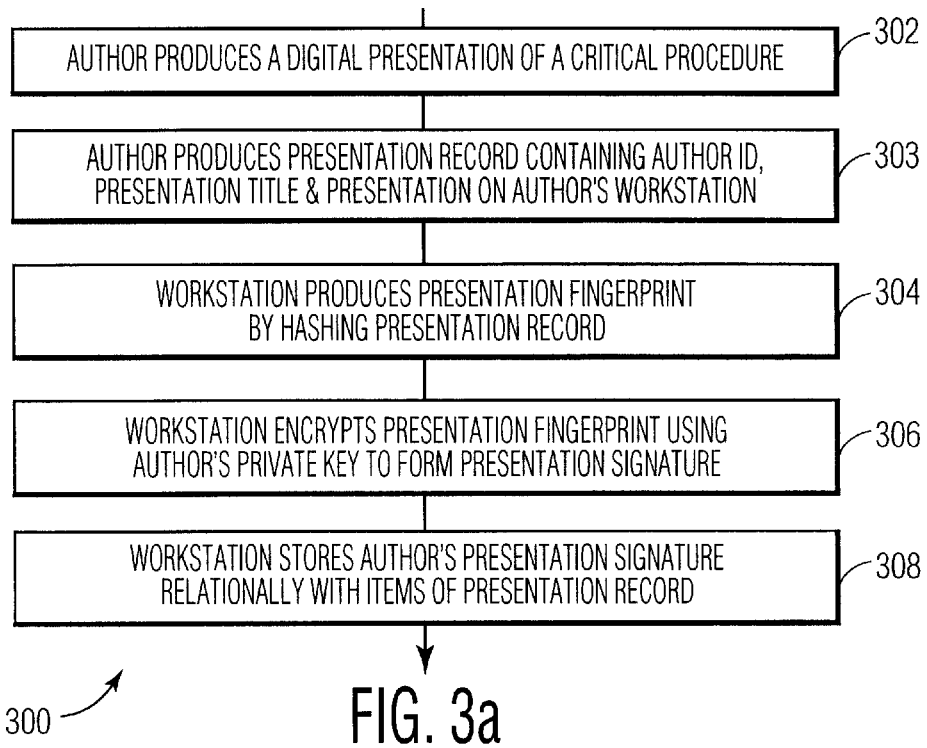
FIGS. 3a–3i illustrate another flow chart for a third specific embodiment of the invention for authenticating presentations of critical procedures and reviews of such procedures.

FIGS. 3a–3i illustrate a third specific embodiment of the invention for authenticating reviews. FIG. 3a shows a first group of steps 300, of the method of the invention in which an author creates a digital presentation that documents the procedure used in a critical process. Then the author uses software loaded in the author's workstation for signing, storing, and having the presentation notarized, so that, others can authenticate the origin and integrity of the presentation and the time of notarizing the presentation.

The presentation may be a multimedia documentary including video, audio, text, images and any other type of digital information about a critical procedure. As an example, the presentation may be an audio video record of an inspection of a building under construction to document compliance with specifications and building codes. The presentation may document the design or construction or testing of a product such as an airplane or a facility such as a nuclear power plant. The presentation may be a record of a procedure such as, a multimedia documentary of a medical procedure such as a medical operation on a patient. The presentation may be created as legal evidence such as a video version of a last will and testament or a video deposition of a witness for a legal proceeding.

In step 302, an author creates the presentation. The presentation may be created using remote mobile equipment (e.g.. a cam corder) and then loaded into the author's workstation or it may be produced at the workstation using connected recording equipment and software loaded onto the author's workstation. When the presentation is ready, the author inputs a command to sign the presentation. In step 303, the author's workstation produces a presentation record containing the presentation and stores the record. Preferably, the presentation record also contains the author's ID and the presentation title. Other information may also be included in the presentation record such as the revision and editing history for creating the presentation, the creation time of the presentation, the workstation ID. Preferably, the items of information in the presentation record are stored relationally so they can easily be retrieved. In step 304, the author's workstation hashes the presentation record using a specified one-way hashing method to form a presentation fingerprint. In step 306, the workstation encrypts the presentation fingerprint using the author's private key (or private key of the workstation) to form the author's signature for the presentation. Finally, in step 308, the workstation stores the author's signature in the storage of the workstation relationally with the items of information in the presentation record.

Figure 3B:
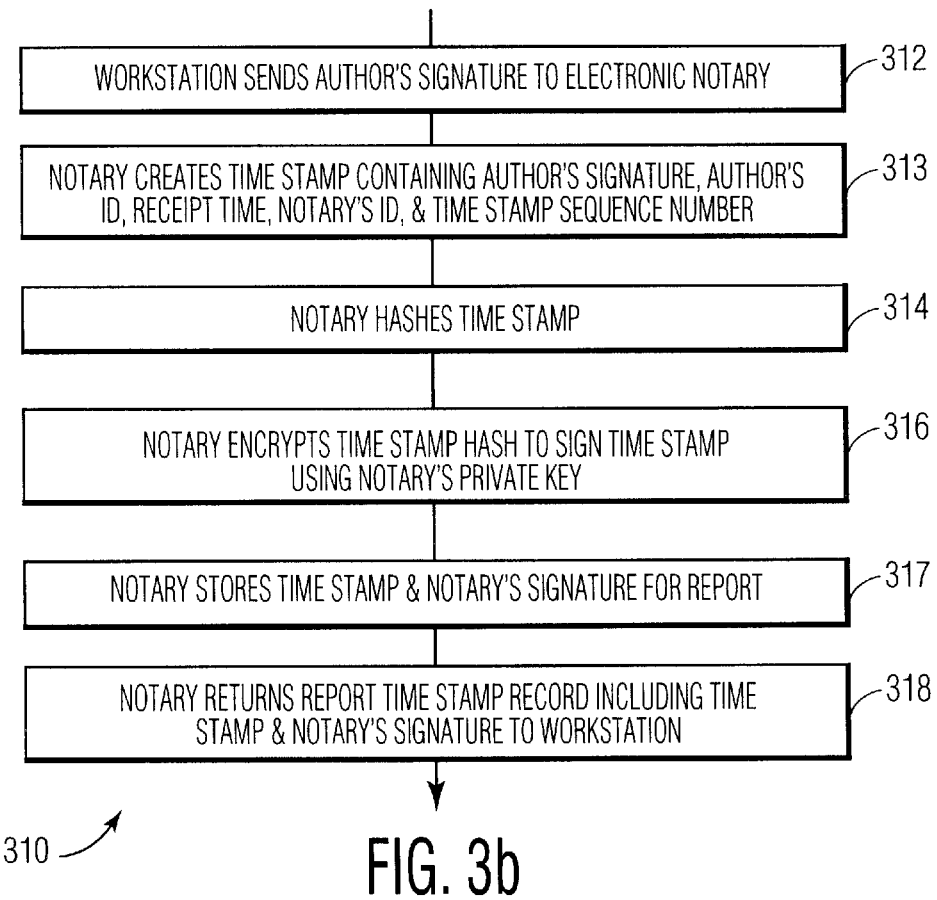

In the second group of steps 310, of the third embodiment the invention in FIG. 3b, the author's workstation obtains a time stamp and time stamp signature for the author's presentation signature, from an electronic notary. In step 312, the author's workstation sends the author's presentation signature to an electronic notary's host system. In step 313, the host creates a time stamp containing the author's signature and the receipt time. Preferably, the notary ID, time stamp sequence number, and author ID are also included in the time stamp. In step 314, the notary hashes the time stamp, and in step 316, the notary signs the time stamp hash using the notary's private key. In step 317, the electronic notary stores the time stamp and the notary's signature for the presentation relationally. In step 318, the notary transmits, to the author, a time stamp record for the presentation, including the presentation time stamp and the notary's presentation signature for the time stamp.

Figure 3C:
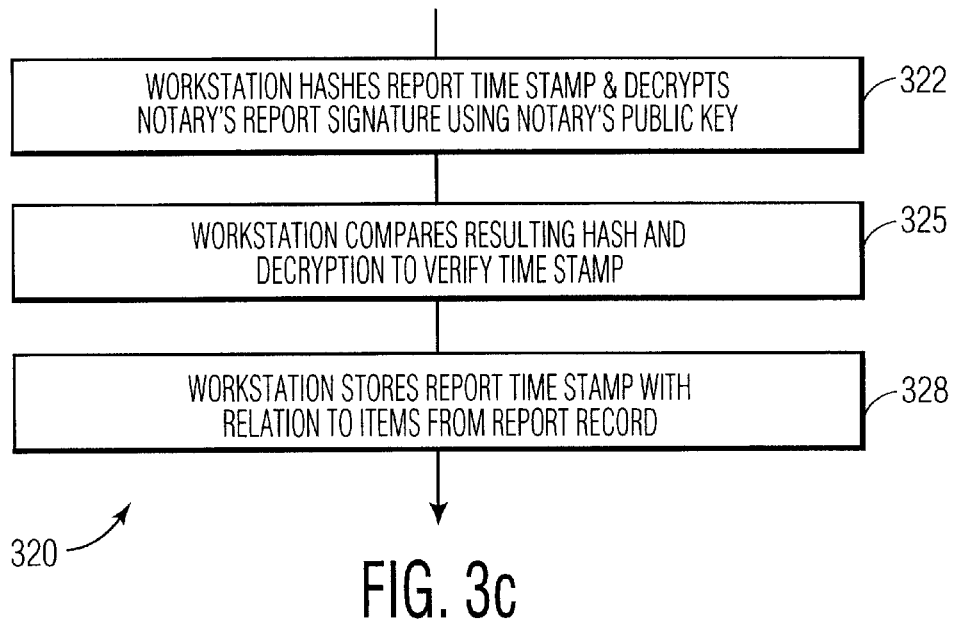
Figure 3D:
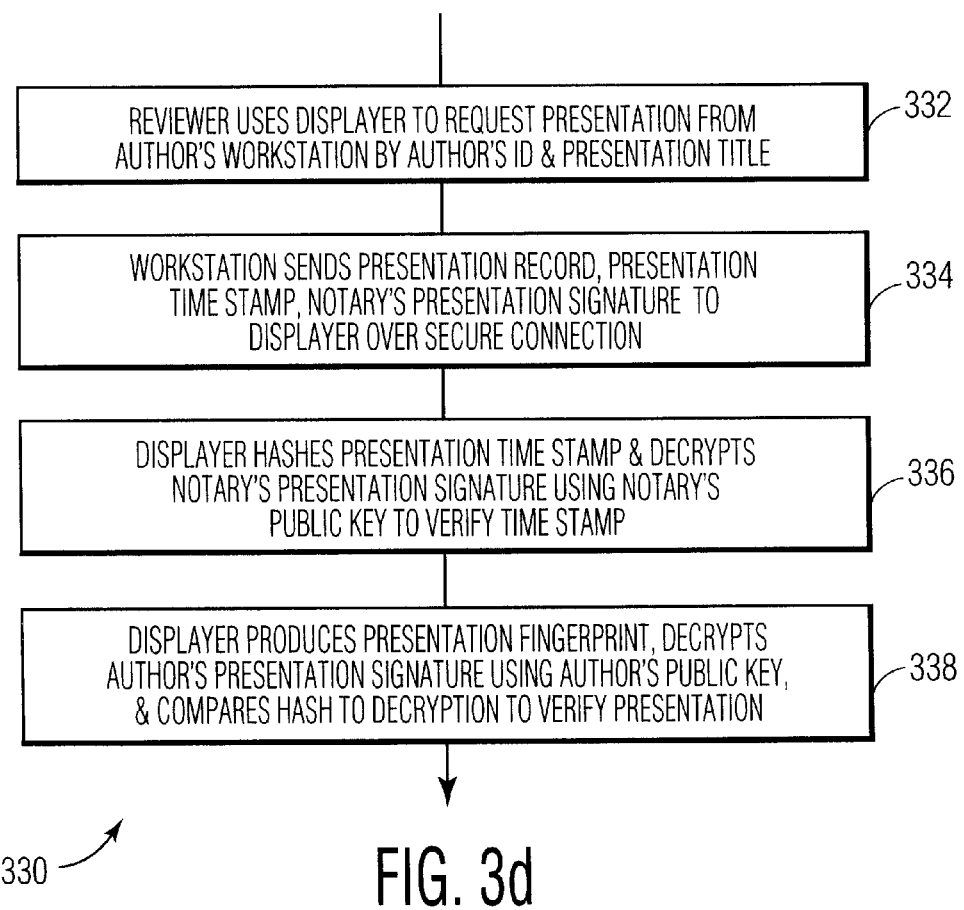

In the next group of steps 320 in FIG. 3c, the author authenticates and stores the time stamp record. In step 322, in order to authenticate the time stamp, the workstation hashes the time stamp and decrypts the notary's signature using the notary's public key. In step 325, the authoring workstation compares the time stamp hash with the decrypted time stamp signature, and if there is a match, then the time stamp is authenticated. In step 328, the workstation stores the information items of the time stamp record and any previous and subsequent time stamp records with relation to the information items in the presentation record.

Figure 3E:
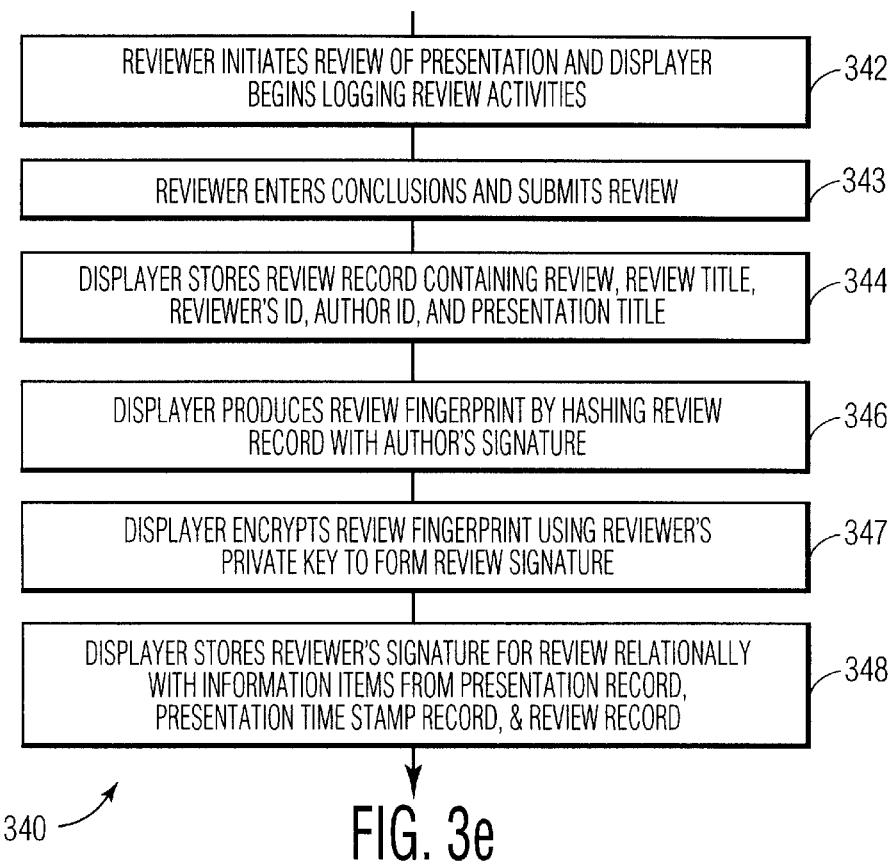

In the next group of steps 330, in FIG. 3e, a reviewer (human user) obtains a copy of the presentation from the author and verifies its origin and integrity. In step 332, the reviewer uses a review workstation (displayer) to request the presentation from the author by specifying the author's ID and presentation title. In step 334, the authoring station sends the presentation record and presentation time stamp record to the displayer. In step 336, the displayer hashes the time stamp and decrypts the notary's signature using the notary's public key to verify the time stamp. In step 338, the workstation reproduces the presentation fingerprint and decrypts the author's signature (contained in the time stamp) using the author's public key and compares the decrypted signature to the fingerprint to verify the presentation.

In the next group of steps 340, in FIG. 3e, of this third embodiment, the reviewer reviews the presentation as a review activity log (review) is automatically produced by the reviewer's workstation in order to document the review process, and the review is digitally signed and stored. In step 342, the reviewer initiates the review of the presentation and the reviewer's workstation (displayer) automatically begins recording the review activities in a log. In step 343, the reviewer enters conclusions of the review of the presentation into the review log and inputs a command to sign the review. In step 344, the displayer creates a review record including the review and preferably the reviewer's ID. The record may also contain the review title, the displayer ID, the author's ID and/or the presentation title. In step 346, the displayer combines the review record and the author's signature and hashes the combination to form a review fingerprint. In step 347, the reviewer's workstation produces the reviewer's signature by encrypting the review fingerprint using the reviewer's private key. In step 348, the displayer stores the reviewer's signature relationally with the information items in the review record, the presentation record, and the presentation time stamp record.

Figure 3F:
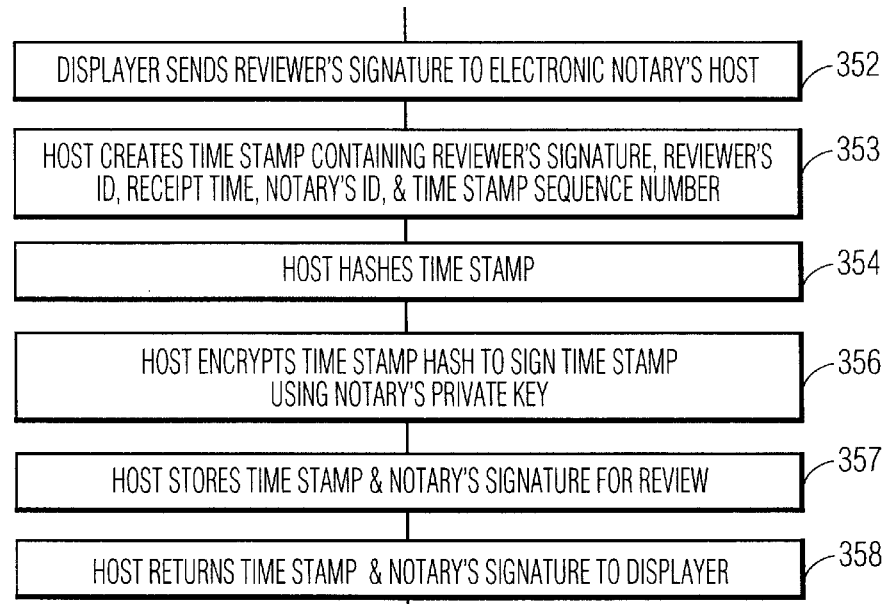

In another group of steps 350, in FIG. 3f, of this third specific embodiment, the displayer sends the reviewer's signature to an electronic notary which produces a time stamp, signs the time stamp, stores the time stamp and its signature and returns the time stamp and signature to the reviewer. These steps are similar to the group 310 of steps in FIG. 3b, for providing the author's signature, which should be referred to and only the differences will be discussed below in detail. In step 352, the displayer sends the reviewer's signature to the host of an electronic notary. In step 353, the host creates a time stamp that contains the reviewer's signature and the receipt time. In step 354, the host hashes the time stamp, and in step 356 the host signs the time stamp by encrypting the hash using the notary's private key. In step 357, the host stores the time stamp and notary's signature, and in step 358, the notary returns a time stamp record including the review time stamp and the notary's review signature to the reviewer's workstation.

Figure 3G:
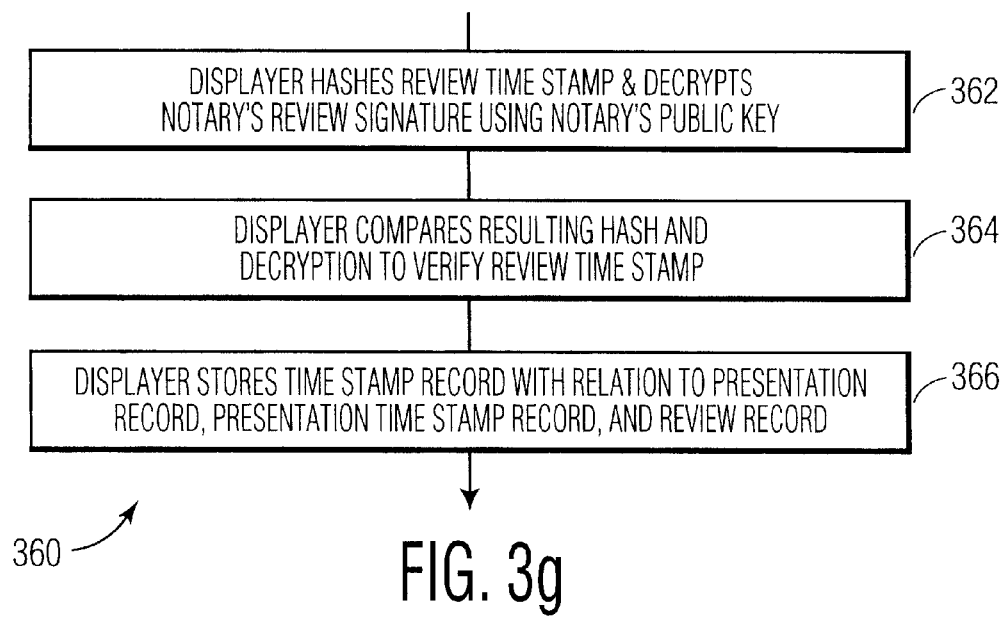

In the next group of steps 360, in FIG. 3g, for this embodiment, the displayer verifies the notary's time stamp and signature for the review, and stores the time stamp record. These steps are similar to steps 320 in FIG. 3c, discussed above, which should be referred to for details, so only the differences will be discussed in detail below. In step 362, the displayer hashes the review time stamp and decrypts the notary's review signature. In step 363, the displayer compares the hash and decryption to verify the review time stamp and notary's review signature. In step 364, the displayer stores the review time stamp and notary's review signature with relation to the information items in the presentation record, presentation time stamp record, and review record.

Figure 3H:
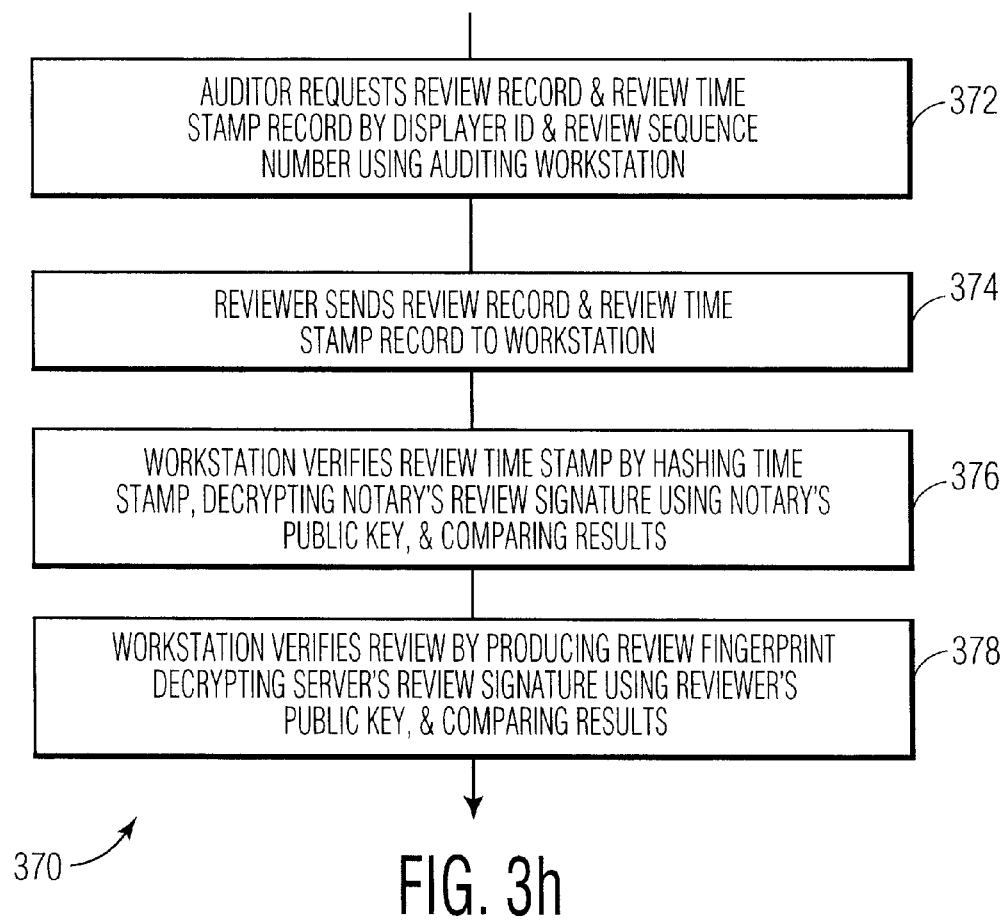

In the next set of steps 370 in FIG. 3h, an auditor (human user) requests the review record and review time stamp record and verifies the review and review time stamp. In step 372, the auditor requests the review and review time stamp from the reviewer using an auditing workstation. In step 374, the reviewer sends the review record and the review time stamp record to the auditor's workstation. In step 376, the workstation hashes the review time stamp and decrypts the notary's review signature using the notary's public key, and compares the hash and decrypted signature in order to verify the digital time of notarization and other information in the presentation time stamp. In step 378, the workstation verifies the review by producing the review fingerprint and decrypting the reviewer's review signature (from the review time stamp) and comparing the decryption with the fingerprint to verify the origin and integrity of the review.

Figure 3I:
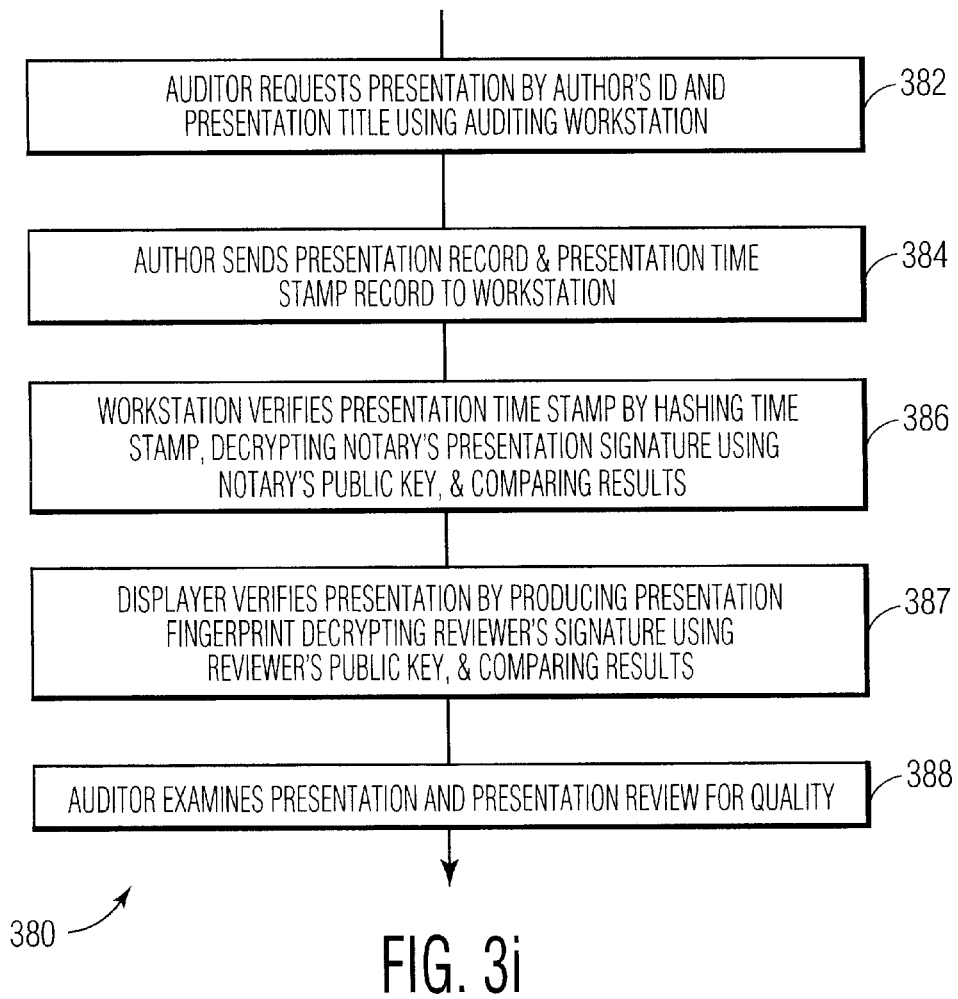

In the final group of steps 380, in FIG. 3i, of this third embodiment, the auditor requests the presentation record and presentation time stamp record, verifies the presentation and presentation time stamp, and then audits the presentation and the review for quality. In step 382, the auditor requests the presentation, and in step 384, the author sends the presentation record and the time stamp record for the presentation to the auditor's workstation. In step 386, the auditor's workstation verifies the presentation time stamp by hashing the presentation time stamp and decrypting the notary's presentation signature using the notary's public key, and comparing the hash to the decryption. In step 387, the workstation produces the presentation fingerprint and decrypts the authors's presentation signature (from the presentation time stamp) and compares the decryption with the fingerprint to verify the origin and integrity of the presentation. Finally in step 388, the auditor plays the review log based on the presentation in order to determine the quality of the presentation and the review of the presentation.

Figure 4:
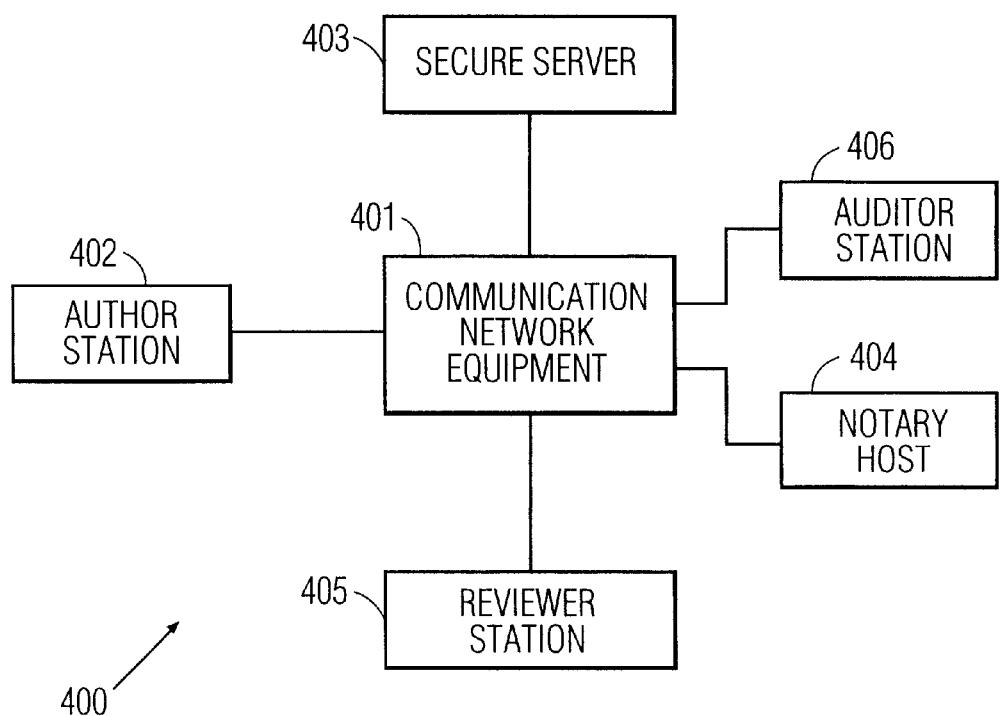
FIG. 4 shows a sample embodiment of the network system of the invention.

FIG. 4 illustrates network 400 of the invention, in which a multitude of computer nodes are connected together by a communications network 401 of cables and communications equipment. The network nodes include one or more authoring stations 402 for creating digital documents, secure server 403 for storing the documents and providing them to the other nodes, host 404 of an electronic notary for time stamping the documents, one or more reviewing station 405 for reviewing the digital documents and automatically creating a review log of the review activities. Also, the network includes one or more auditing stations 406 for auditing the quality of the documents and for auditing the quality of the reviews of the documents. All the nodes may be provided by programming general purpose computer workstations and providing equipment required for specific functions, for example, if an authoring station is intended for producing x-ray images then an x-ray imager will have to be provided and connected to the workstation for use in such authoring.

The authoring stations include equipment and other apparatus (e.g. programmed memory) for creating documents and may also include apparatus for signing the documents and/or for obtaining time stamps for the documents from the notary's host. The documents may be audio or video images such as pictures, medical scans, text images, and dictations. The documents may include revisions of previous document. The documents may be reports including multiple text pages, images, and/or audio records in combination. The authoring stations may include apparatus for creating multimedia presentations, for example, of critical process. An authoring station may include audio and video equipment for producing such multimedia presentations or merely means for downloading information produced by mobile equipment such as video camcorders. The authoring stations also include apparatus for transmitting the documents to the server or to the reviewing station and auditing station, and may include apparatus for receiving documents to include in the digital documents or for revising such documents.

Figure 5:
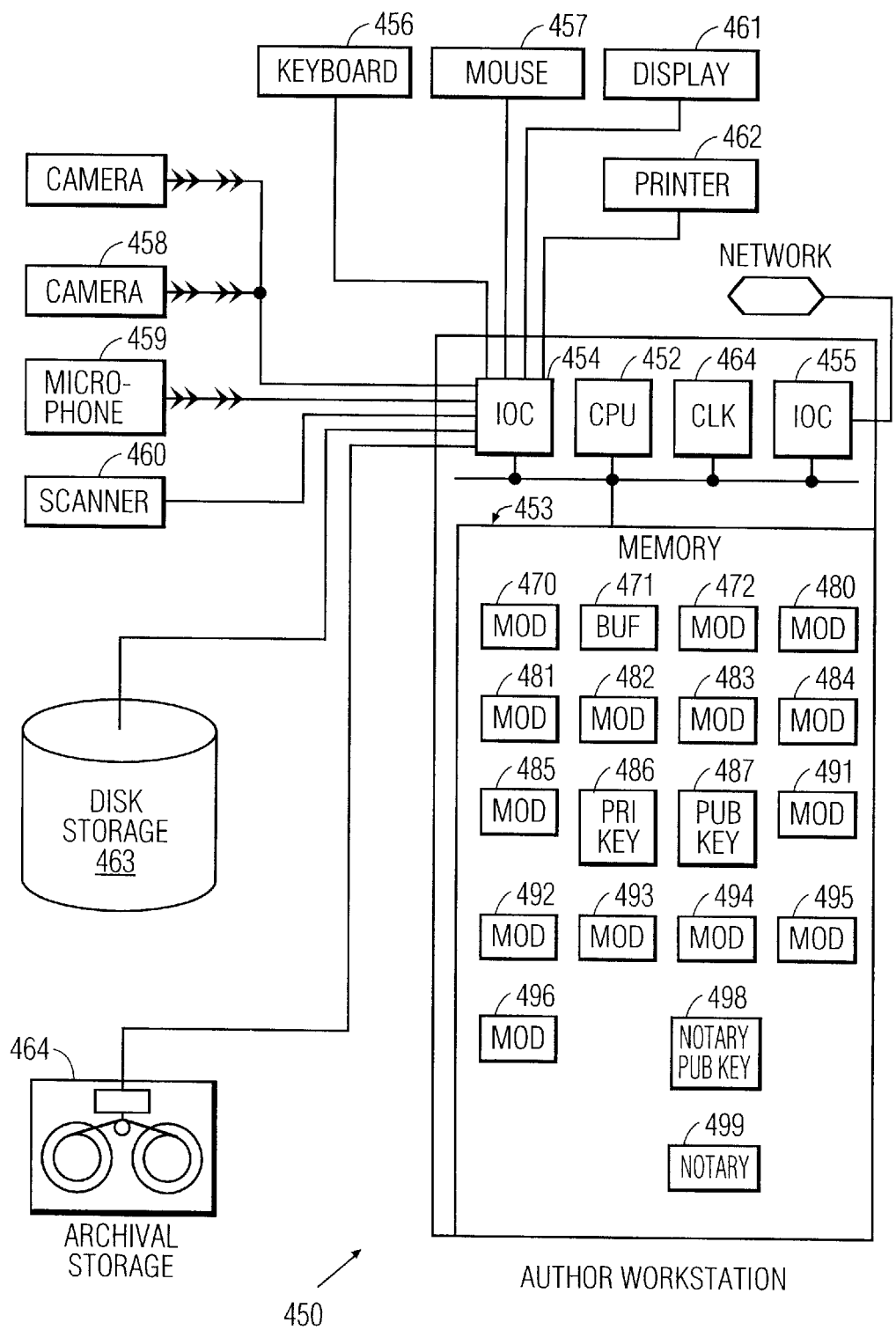
FIG. 5 provides additional details of the authoring workstations of FIG. 4.

In FIG. 5, additional details of authoring station 450 are shown. The authoring station includes processor 452 such as a central processing unit (CPU) or an embedded controller, communicating with electronic memory 453. The memory includes program modules which control the operation of the processor and buffers for storing information received or to be transmitted through input and/or output circuit (IOC) 454 between the buffers and authoring station peripherals and through IOC 455 between the buffers other nodes of the network. The peripherals may include input apparatus, for example, keyboard 456, mouse 457 (or other pointer), video camera 458, microphone 459, and scanner 460, and output equipment such as display 461 and printer 462. The peripherals may also include storage equipment such as disk storage 463 and archival storage 464 (such as a tape drive or RW-ROM).

The memory includes program module 470 for operating IOC 454 for moving information from buffer 471 to the peripherals and storing information received from the peripherals into buffer 471. The memory also includes program module 472 for operating IOC 455 for moving information from buffer 471 to other nodes of the network and for storing information received from the other nodes into buffer 471.

In the specific embodiment shown in FIG. 5, the authoring workstation includes authoring apparatus 480 for use by an author to produce a first document. The authoring apparatus may include apparatus 481 for producing an image, apparatus 482 for producing a report, and/or apparatus 483 for producing a multimedia production for documenting the steps preformed during a critical procedure. Apparatus 484 is provided for producing a first document record containing the first document. The document record may also contain information identifying the author, the authoring workstation, the time of the authoring, the time of signing, the identification of other documents on which the first document depends, a sequence number of the document, and a title of the document. The authoring station also includes apparatus 492 for storing the first document record, at least until a receipt is received from a server, and apparatus 496 for distributing to others, the first document record.

In the second and third embodiments of the methods of the invention above, the author's workstation signs the document before distributing the document, and then distributes the document signature along with the document. For that reason, this embodiment of the authoring station includes apparatus 485 for producing a fingerprint of the first document record using a one-way hashing method. Private key 486 is used for encrypting the fingerprint of the first document to produce a first document signature and the first document private key is kept confidential and can not be accessed by others. Apparatus 491 produces a first document signature by encrypting the first document fingerprint using first document private key 486, and public key 487 is used for decrypting the first document signature. The public key is distributed to others by the author workstation, server 403, or otherwise. Also, apparatus 492 is adapted for storing the first document signature relationally with the information items of the first document record, and apparatus 496 is adapted for distributing to others, the first document signature and public key 487 which may be used for decrypting the first document signature.

In the third embodiment of the method of the invention described above, the authoring station obtains a time stamp and time stamp signature for the first document and distributes these along with the first document and the first document signature. Apparatus 493 provides the first document signature to an electronic notary. The notary may be a portion of the authoring workstation 499 which is secure from the author, and preferably secure from the owner of the workstation. On the other hand, the notary may be a remote host connected, for example, by a telephone system and modem to the authoring workstation or server. Apparatus 494 obtains a time stamp and a time stamp signature from the electronic notary for the first document. The time stamp contains the first document signature and a digital time when the time stamp was produced. The first document time stamp signature is produced by encrypting a fingerprint of the first document time stamp using private key 498 of the notary. The fingerprint of the review document time stamp is produced by hashing the first document time stamp using a one-way hashing method. Apparatus 495 stores the first document time stamp and the first document time stamp signature of the notary. Apparatus 496 distributes to others, the first document time stamp and the first document time stamp signature. The notary also provides public key 498 to others, for decrypting the first document time stamp signature.

The reviewing stations are used to request digital documents, to review the documents while automatically producing a log of review activities (i.e. a review), and to transmit the reviews, for example, to a server for storage or to an auditing station as described below. The documents to be reviewed (first documents) may be obtained from the server or from the author's workstation, and the resulting reviews may be transmitted to the server or to the auditor's workstation. The review station may include apparatus for signing reviews and/or for obtaining time stamps for the reviews from the notary's host.

Figure 6:
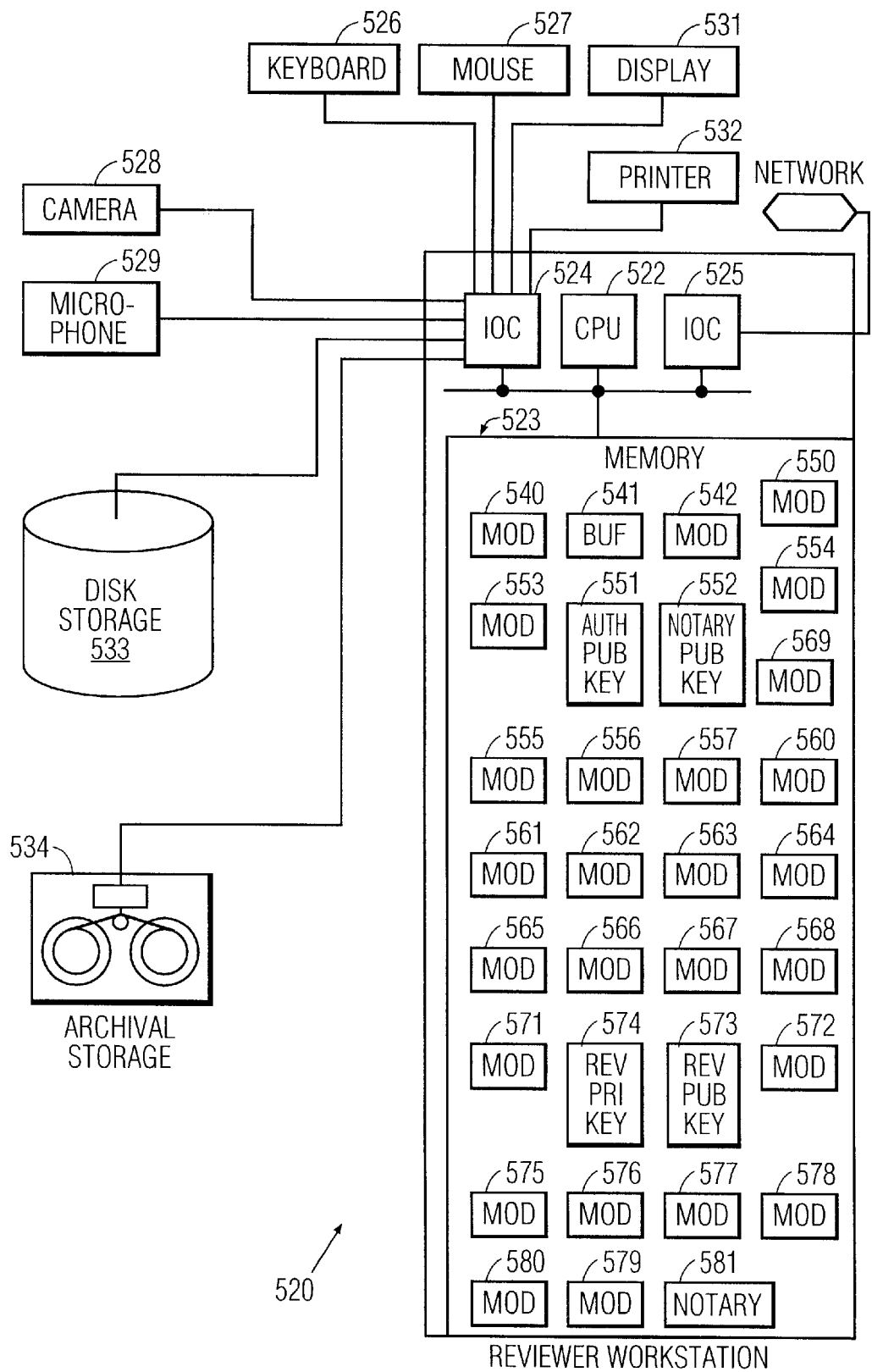
FIG. 6 provides additional details of the reviewing workstations of FIG. 4.

In FIG. 6, additional details of reviewing station 520 are shown. The reviewing station includes processor 522 communicating with electronic memory 523. The memory includes programs (programmed memory) which control the operation of the processor and which contains buffers for storing information received or to be transmitted through input and/or output circuit (IOC) 524 between the buffers and reviewing station peripherals and through IOC 525 between the buffers and other nodes of the network. The peripherals may include input apparatus, such as, keyboard 526, mouse 527 (or other pointer), video camera 528, microphone 529, and may include output equipment, such as, display 531 and printer 532. The peripherals may also include storage equipment such as disk storage 533 and archival storage 534 (such as a tape drive or RW-ROM).

Memory 523 includes program module 540 for operating IOC 524 for moving information between buffer 541 and the peripherals for input, output, and storage. The memory also includes program module 542 for operating IOC 545 for moving information between buffer 541 and other nodes of communications network 400.

The memory includes apparatus 550 for obtaining the first document record, the first document time stamp, the first document time stamp signature, first document public key 551 for decrypting first document signatures, and notary's public key 552 for decrypting time stamp signatures.

The review station verifies the first document and first document signature. Apparatus 553 decrypts the first document signature using first document public key 551, and apparatus 554 reproduces the fingerprint of the first document using the one-way hashing method. Apparatus 555 compares the first document fingerprint with the decryption of the first document signature and verifies the origin of the first document and that the first document has not been altered since it was signed, depending on the comparison.

Similarly, the review station verifies the time stamp and time stamp signature that was received. Apparatus 556 reproduces the fingerprint of the first document time stamp by hashing the time stamp using the one-way hashing method, and apparatus 557 decrypts the first document time stamp signature using public key 552 of the notary. Apparatus 560 compares the first document time stamp fingerprint with the decryption of the first document time stamp signature and verifies the origin of the first document time stamp and that the first document time stamp has not been altered since it was signed, depending on the comparison.

Apparatus 561 automatically creates a review document while a human reviewer reviews the first document. The review document includes a record log of the activities of the reviewer during the review and may include other information relevant to the review. Apparatus for creating the review document may include one or more of: apparatus 562 for recording information indicating the periods of time for which a portion of the first document was displayed, apparatus 563 for recording information indicating the order in which multiple portions of the first document were displayed, apparatus 564 for recording information indicating the periods of time when the reviewer was looking at each of multiple respective windows or displays, apparatus 565 for recording information indicating the order in which the reviewer looked at respective windows or displays, apparatus 566 for recording information entered by the reviewer, apparatus 567 for recording the configuration of the software of a review workstation, apparatus 568 for recording configuration of the hardware of the review workstation, and apparatus 569 for recording information indicating image manipulations performed during the review.

Apparatus 571 produces a review document record containing the review document and information for identifying the first document on which the review is based. The identifying information may be information in the first document record, information in the first document time stamp, and/or information in both. The review document record may also contain one or more of: the identity of the reviewer, the identity of the reviewer workstation, the time of the review, a sequence number for the review, and a title for the review. Apparatus 576 stores the review document record and apparatus 580 distributes the review document record to others. In the first and second embodiments of the method of the invention, described above the review station distributes the review document only to the server, but in the third embodiment the reviewer station distributes the review document directly to an auditor.

In the second and third embodiments of the method of the invention above, the reviewer's workstation signs the review and distributes the review signature and a public key for decrypting the review signature. In this case, apparatus 572 produces a fingerprint of the review document record using a one-way hashing method. Review private key 574 is used for encrypting the fingerprints of review documents to produce review signatures and can not be accessed by others, and apparatus 575 produces a review document signature by encrypting the review document fingerprint using the review private key. Apparatus 576 stores the review document signature. Review public key 573 is used for decrypting review signatures. Apparatus 580 distributes, to others, public key 573 and the review document signatures.

Figure 8:
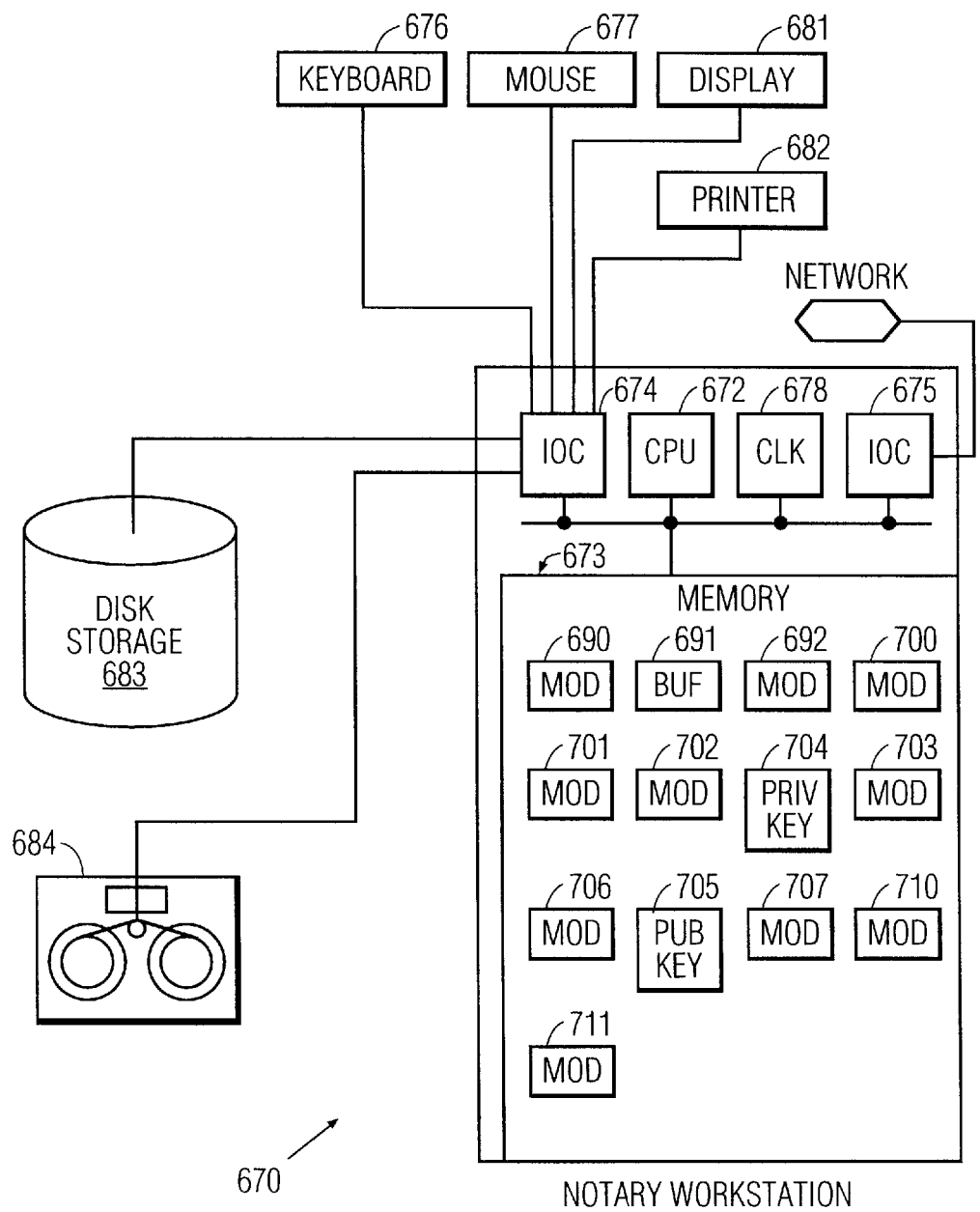
FIG. 8 illustrates additional details of the notary's host of FIG. 4.

In the third embodiment of the method of the invention described above, the reviewer's station obtains a time stamp for the review from a notary. The notary may be portion 581 of the workstation or a separate node of the network as shown in FIGS. 4 and 8. Apparatus 577 provides the review signature to an electronic notary. Then apparatus 578 obtains a time stamp and a time stamp signature from the electronic notary for the review document. The time stamp contains the review signature and a digital time when the time stamp was produced. The review time stamp signature is produced by encrypting a fingerprint of the review time stamp using private key 704 (in FIG. 8) of the notary. The fingerprint of the review time stamp is produced by hashing the review time stamp using a one-way hashing method. Apparatus 579 stores the review time stamp and the review time stamp signature of the notary, and apparatus 580 distributes, to others, the review time stamp and the review time stamp signature.

The auditing stations are used for requesting the digital documents and respective reviews of the documents and auditing the quality of the documents and the quality of the reviews. The same workstations may be used for authoring, reviewing, and auditing if all the required hardware and other apparatus is provided on the workstation.

Figure 7:
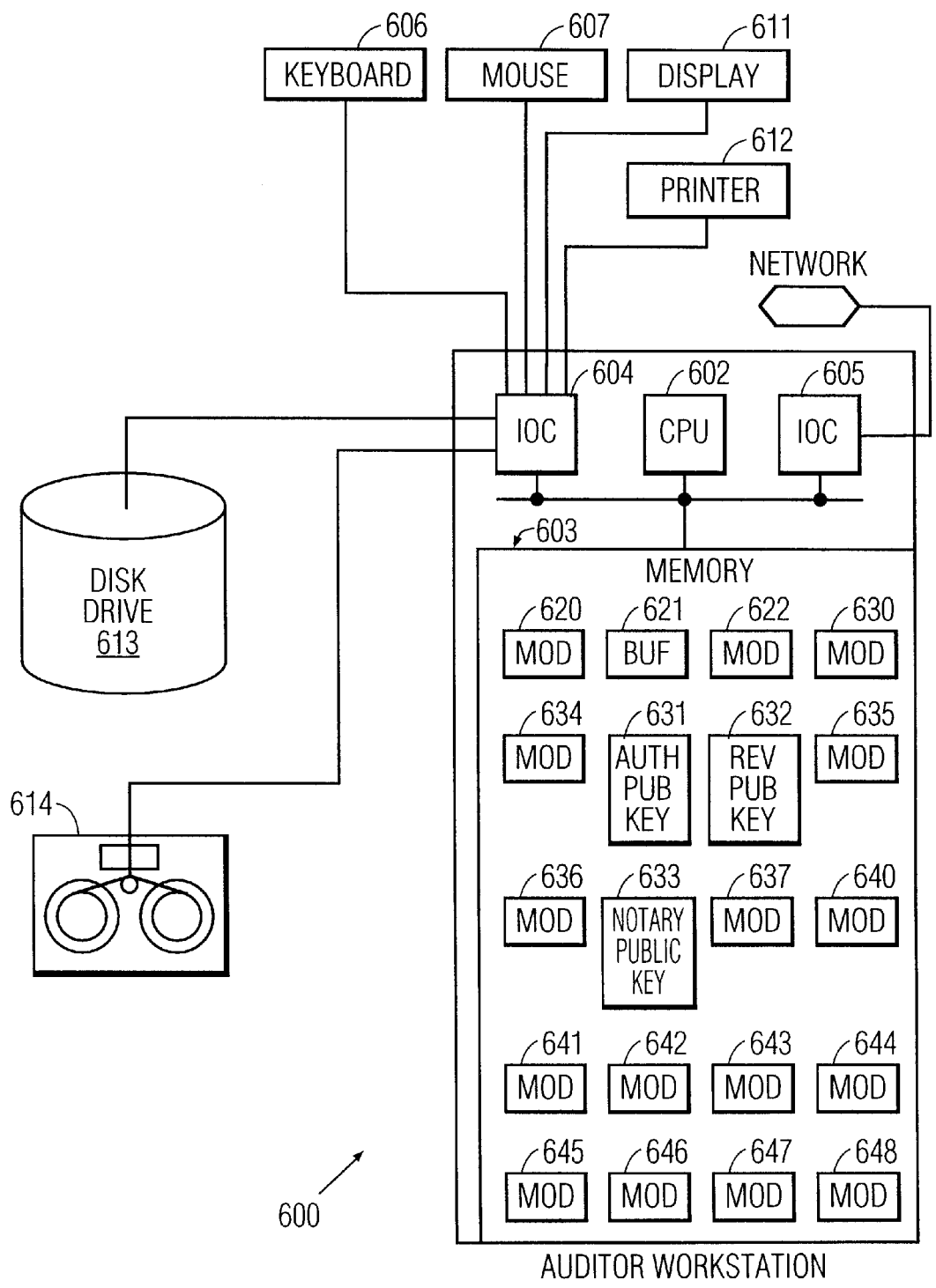
FIG. 7 illustrates additional details of the auditing workstations of FIG. 4.

In FIG. 7, additional details of a auditor's workstation 600 are shown. The auditing station includes processor 602 communicating with electronic memory 603. The memory includes program modules (programmed memory) which control the operation of the processor and contains buffers for storing information received or to be transmitted through input and/or output circuit (IOC) 604 between the buffers and auditing station peripherals and through IOC 605 between the buffers and other nodes of the network. The peripherals may include input apparatus, such as, keyboard 606, mouse 607 (or other pointer), and may include output equipment, such as, display 611 and printer 612. The peripherals may also include storage equipment such as disk storage 613 and archival storage 614.

Memory 603 includes program module 620 for operating IOC 604 for moving information between buffer 621 and the peripherals for input, output and storage. The memory also includes program module 622 for operating IOC 605 for moving information between buffer 621 and other nodes of communications network 400.

In the memory, apparatus 630 obtains the first document record, the first document signature, the first document public key 631 (for decrypting the first document signature), the first document time stamp, the first document time stamp signature, the notary's public key 633 (for decrypting the time stamp signature), the review record, the review document signature, the reviewer's public key 632 (for decrypting the review signature), the review document time stamp, and the review time stamp signature.

The auditing workstation verifies the first document and first document signature. Apparatus 634 decrypts the first document signature using the author's public key 631, and apparatus 635 reproduces the fingerprint of the first document using the one-way hashing method. Apparatus 636 compares the first document fingerprint with the decryption of the first document signature and verifies the origin of the first document, based on the comparison. Herein, verification means proving that the first document was produced by the author and has not been altered since it was signed.

The auditing workstation then verifies the first document time stamp. Apparatus 637 produces the fingerprint for the first document time stamp by hashing the time stamp using the one-way hashing method, and apparatus 640 decrypts the first document time stamp signature using the notary's public key 633. Also, apparatus 641 compares the fingerprint with the decryption of the signature and verifies the origin of the first document time stamp and that the first document time stamp has not been altered since it was signed, depending on the comparison.

Then the auditing workstation verifies the review document and review document signature. Apparatus 642 decrypts the review document signature using the reviewer's public key 632, and apparatus 643 reproduces the fingerprint of the review document using the one-way hashing method. Apparatus 644 compares the review document fingerprint with the decryption of the review document signature and verifies the origin of the review document and that the review document has not been altered since it was signed, depending on the comparison.

Then the auditing workstation verifies the review time stamp. Apparatus 645 produces the fingerprint for the review time stamp by hashing the time stamp using the one-way hashing method. Apparatus 646 decrypts the review time stamp signature using public key 633 of the notary. Apparatus 647 compares the review time stamp fingerprint with the decryption of the review time stamp signature and verifies the origin of the review time stamp and that the review time stamp has not been altered since it was signed, depending on the comparison.

Finally, apparatus 648 is used by the auditor for determining the quality of the first document and the quality of the review of the first document.

The notary's host receives signatures for documents and creates a time stamp including the document signature and a notarizing time. The host may receive the requests for time stamps only from the secure server or may receive them from the reviewing station and auditing station. The electronic notary provides the time stamps, so that, others can verify that a document signature existed at the time of notarization, and therefore, that the document existed before that time. The host may simply store the time stamp, but preferably, also returns the time stamp to the requesting party. A notary's signature for the time stamp may also be provided. The notary may also be involved in authenticating the time stamps as described below.

In FIG. 8, additional details of a notary's workstation 670 are shown. The notarizing station includes processor 672 communicating with electronic memory 673. The memory includes programs (programmed memory) which control the operation of the processor and contains buffers for storing information received or to be transmitted through input and/or output circuit (IOC) 674 between the buffers and notarizing station peripherals and between the buffers and other nodes of the network. The peripherals may include input apparatus, such as, keyboard 676, mouse 677 (or other pointer), and may include output equipment, such as, display 681 and printer 682. The peripherals may also include storage equipment such as disk storage 684 and archival storage 683. Clock 678 provides stamping times for the time stamps provided by the notary.

Memory 673 includes program module 690 for operating IOC 674 for moving information between buffer 691 and the peripherals for input, output and storage. The memory also includes program module 692 to operate IOC 675 for moving information between buffer 691 and other nodes of communications network 400.

First the notary's host uses apparatus 700 to receive a document signature from a customer such as a server, author or reviewer. Then the host creates a time stamp and signs the time stamp. Apparatus 701 determines a stamping time based on clock 678. Apparatus 702 produces a time stamp containing the document signature and the stamping time. The time stamp preferably, also contains one or more of: the identity of the customer, a sequence number of the time stamp, and the identity of the notary. Apparatus 703 produces a fingerprint of the time stamp by hashing the time stamp using a one-way hashing method.

Private key 704 of the notary is used for encrypting the time stamp fingerprint and the private key is protected, to prevent access by others. Apparatus 706 produces a time stamp signature by encrypting the time stamp fingerprint using private key 704 of the notary. Public key 705 of the notary is used by others for decrypting the time stamp signature that was encrypted using the private key.

The host stores the time stamp and returns it to the customer. Apparatus 707 stores the time stamp and the time stamp signature relationally in a disk storage system of the notary. Apparatus 710 returns the time stamp and time stamp signature to the customer. Also, apparatus 711 distributes the notary's public key 705 to others whereby others may verify that the time stamp is from the notary and has not been altered since it was signed, and thus the information in the time stamp is accurate at least according to the notary.

The secure server includes apparatus for storing and retrieving documents and may include apparatus for signing documents and for obtaining time stamps for documents from the notary's host.

Figure 9:
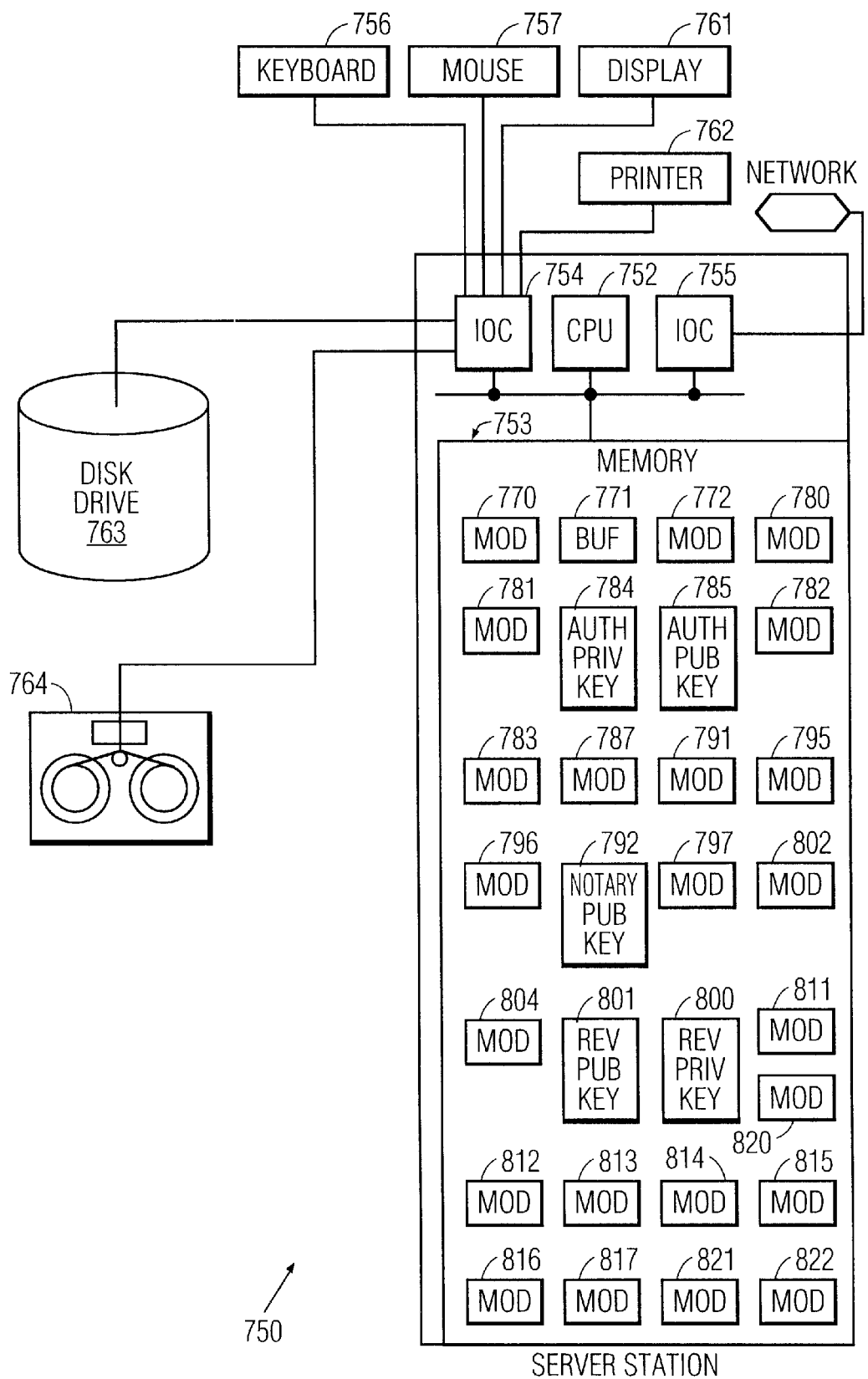
FIG. 9 shows additional details of the secure server of FIG. 4.

In FIG. 9, additional details of a customer's server 750 are shown. The server station includes processor 752 communicating with electronic memory 753. The memory includes programs (programmed memory) which control the operation of the processor and contains buffers for storing information received or to be transmitted through input and/or output circuit (IOC) 754 between the buffers and server peripherals and through IOC 755 between the buffers and other nodes of the network. The peripherals may include input apparatus, such as, keyboard 756, mouse 757 (or other pointer), and may include output equipment, such as, display 761 and printer 762. The peripherals may also include storage equipment such as disk storage 763 and archival storage 763.

Memory 753 includes program module 770 for operating IOC 754 for moving information between buffer 771 and the peripherals for input, output and storing information. The memory also includes program module 772 for operating IOC 755 for moving information between buffer 771 and other nodes of communications network 401.

In the third embodiment of the method of the invention above, a server is not described, however, a server could be used in that embodiment, if convenient, to receive and store information and then provide the information to others. The server may provide information related to the first document and/or information related to the review of the first document.

In order to provide information related to the first document, the server includes apparatus 780 for receiving through a secure channel, a first document from the author. Apparatus 780 may receive a first document record from an author or apparatus 781 may be provided for producing a first document record. The first document record includes the first document and may also include other information such as the author ID, author's workstation, document title, creation date, sequence number of the first document. Apparatus 782 stores the first document record. Apparatus 811 may be provided for producing a digital signature for the first document. The signature is formed by encrypting the first document fingerprint using a first document private key 784. The digital signature for the first document may be provided by receiving the signature from the author or by forming and encrypting a digital fingerprint using a first document private key 784 of the server, author, or author's workstation. A first document public key 785 is used by others for decrypting the signature of the first document for reproducing the first document fingerprint. Apparatus 787 distributes the first document record, the first document signature, and the first document public key 785 whereby others can decrypt the first document signature using the public key, produce the first document fingerprint by hashing the time stamp, and compare the decryption with the fingerprint to verify the origin and integrity of the first document.

The server may also provide to others, a time stamp and time stamp signature for the first document. Apparatus 815, 816, 817 provides a time stamp and time stamp signature of a notary for the first document. The time stamp and time stamp signature for the first document may be furnished by the author, or the server may obtain the time stamp and time stamp signature for the first document by sending the first document signature to an electronic notary and receiving the time stamp and time stamp signature back from the notary. Apparatus 791 distributes the time stamp and the time stamp signature for the first document, whereby others can decrypt the time stamp signature using public key 792 of the notary, produce the time stamp fingerprint by hashing the time stamp, and compare the decryption with the fingerprint to verify the origin and integrity of the time stamp and the stamping time in the time stamp.

Similarly, the server may provide information related to the review document. Apparatus 795 receives through a secure channel, a review document. Apparatus 795 may receive a review document record or apparatus 796 may be provided to produce a review document record, containing the review document. Apparatus 813, 814 provides a digital signature for the review document. The signature is formed by encrypting the review document fingerprint using a review document private key 800. The signature includes identifying information for determining whether the review document is based on the first digital document. The identifying information may be based on information in the review document record or in the review time stamp. The digital signature for the review document may be provided by receiving the signature from the reviewer or by encrypting the digital fingerprint using a review private key 800 of the server, reviewer or reviewer's workstation. Review public key 801 is used by others for decrypting the signature of the review document to reproduce the review document fingerprint. Apparatus 802 distributes the review document record, the review signature, and the review public key 801, whereby others can decrypt the review signature using the review public key, produce the review fingerprint by hashing the review record, and compare the decryption with the fingerprint to verify the origin and integrity of the review document and that the review document is based on the first document.

The server may also provide, to others, a time stamp and time stamp signature for the review document. The time stamp and time stamp signature for the review document may be furnished by the reviewer, or the server may obtain the time stamp and time stamp signature for the review document by providing the review document signature to an electronic notary and obtaining the time stamp and time stamp signature from the notary. Apparatus 821, 822 may obtain a time stamp and time stamp signature of a notary for the review document. The notary may be a part of the server or may be a separate node of network 400, as shown in FIGS. 4 and 8. Apparatus 804 distributes the time stamp and time stamp signature whereby others can decrypt the time stamp signature using public key 792 of the notary, produce the time stamp fingerprint by hashing the time stamp, and compare the decryption with the fingerprint to verify the origin and integrity of the time stamp and the stamping time in the time stamp.

The apparatus for providing a first document signature includes one or more of: apparatus 811 for forming first document signatures, and apparatus 812 for receiving a first document signature from the author. The apparatus for forming the first document signature include apparatus 783 for producing a digital fingerprint for the first document by hashing the first document record using a one-way hashing method, and a private key 784 kept confidential in the server for signing the first document by encrypting the fingerprint for the first document.

Similarly, the apparatus for providing a review document signature may include: apparatus 813 for forming a review document signature or apparatus 814 for receiving a first document signature from the reviewer. The apparatus for forming the review document signature may include apparatus 797 for producing a digital fingerprint for the review document by hashing the review document record using a one-way hashing method, and private key 800 is kept confidential in the server, for signing the review document by encrypting the fingerprint for the review document.

The apparatus for providing a time stamp and time stamp signature of a notary for the first document, includes one or more of: apparatus 815 for receiving the time stamp and time stamp signature for the first document from the author; and the combination of: apparatus 816 for providing the first document signature to an electronic notary; and apparatus 817 for receiving a first document time stamp and first document time stamp signature from the electronic notary. The first document time stamp includes the stamping time at which the time stamp was produced and also includes the first document signature. The first document time stamp signature is produced from a fingerprint of the first document time stamp using private key 704 of the notary.

Similarly, the apparatus for providing a time stamp and time stamp signature of a notary for the review document, includes one or more of: apparatus 820 for receiving the time stamp and time stamp signature for the first document from the author; and the combination of: apparatus 821 for providing the review document signature to an electronic notary; and apparatus 822 for receiving a time stamp and time stamp signature for the review document from the electronic notary. The review document time stamp includes the stamping time at which the time stamp was produced and the review document signature. The review document time stamp signature is produced from a fingerprint of the review document time stamp using private key 704 of the notary. The fingerprint of the review document time stamp is produced by hashing the time stamp using a one-way hashing method.

Figure 10:
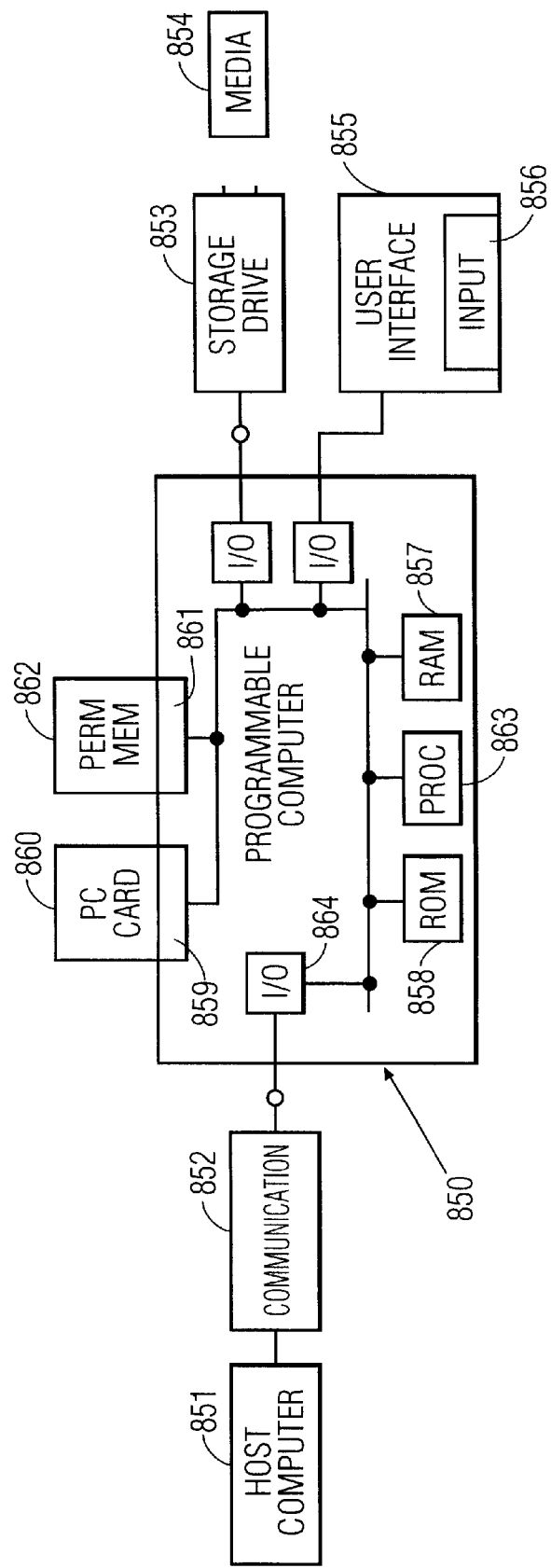
FIG. 10 shows a specific embodiment of apparatus to program the systems of FIGS. 6–9.

FIG. 10 illustrates programmable computer system 850 and various example apparatus for programming such programmable computer which are all well known in the art. The computer system may be programed either by connecting non-volatile memory (e.g. ROM, PROM, EEPROM, flash memory, battery backed SRAM) containing programmed structures, to the programmable computer or by providing signals to the programmable computer which may be applied to memory 857 of the programmable computer in order to provide programmed structures. Another computer system 851 such as an Internet server may be connected through communication apparatus 852 to system 850, so as to provide signals that are used for programming system 850. Apparatus 852 may include a copper or optic cable, radio, infrared, or network such as Ethernet, ARCnet, Token ring, or a modem and telephone system. Storage drive 853 may have integral media 854 and be removably attached to system 850 or drive 853 may be integral with system 850 and receive signals from removable computer media 854. System 850 may include user interface 855 and program input module 856, and written materials may be provided for manually programming the computer. A user may input the signals using apparatus (not shown) of the user interface such as a keyboard, text scanner, microphone, digital camera or bar code reader. The signals provided to system 850 may be copied to storage drive 853 for later recall into volatile memory 857 or stored in non-volatile memory 858 to provide programed apparatus in memory. Alternately, the system may be programmed by providing programmed non-volatile memory. System 850 may include slot 859 to which cartridge 860 containing non-volatile memory such as a PC flash memory card, may be connected to provide programed apparatus. System 850 may include socket 861 into which non-volatile memory package 862 may be inserted to provide programmed apparatus. System 850 may be fabricated with non-volatile integral memory 858 to provide programmed apparatus. The programmed structures include programs and other data in memory which control micro-processor 863 and I/O processors (e.g. 864) of the programmable computer to implement computer processes. The computer system may be a workstation, modem, PC card, printer, or other software ungradable component. Other well known methods of programming a computer system may also be used.

The invention has been described with reference to specific embodiments including the best mode for carrying out the invention, and with sufficient detail that anyone skilled in the art can make and use the invention. Those skilled in the art may modify these embodiments or provide other embodiments within the spirit of the invention, and thus, the description does not limit the present invention to the disclosed embodiments. The invention is limited only by the following appended claims.

I claim:

1. A reviewer workstation, comprising:
   means for receiving through a secure channel, a first document produced by an author;
   means for receiving from a host system of an electronic notary separate from that of the reviewer workstation, a time stamp and time stamp signature for the first document, the first document time stamp containing the stamping time at which the time stamp was produced and a first document signature, the first document time stamp signature being produced by encoding a fingerprint of the first document time stamp using a private key of the electronic notary; and
   means for automatically creating a review document while a human reviewer reviews the first document, including a log of the activities of the reviewer during the review.

2. The reviewer workstation of claim 1 in which:
   the workstation further comprises means for verifying the origin and integrity of the first document, including:
      means for providing: a record for the first document, the record including the first document; and an electronic signature for the first document, the signature being produced using a private key of the first document for encrypting a fingerprint of the first document, the fingerprint being produced by hashing the record of the first document, the hashing being performed using a one-way hashing method;
      a public key of the first document;
      means for decrypting the first document signature using the public key of the first document;
      means for reproducing the fingerprint of the first document using the one-way hashing method; and
      means for comparing the first document fingerprint with the decryption of the first document signature and verifying the origin of the first document and that the first document has not been altered since it was signed, depending on the comparison.

3. The reviewer workstation of claim 2 further comprising:
   means for verifying that the first document signature existed at some particular previous time, including:
      the fingerprint being produced by hashing the time stamp using a one-way hashing method; and
      means for verifying the time stamp including:
         a public key of the notary;
         means for producing the fingerprint for the first document time stamp by hashing the time stamp using the one-way hashing method;
         means for decrypting the first document time stamp signature using the public key of the notary; and
         means for comparing the first document time stamp fingerprint with the decryption of the first document time stamp signature and verifying the origin of the first document time stamp and that the first document time stamp has not been altered since it was signed, depending on the comparison.

4. The reviewer workstation of claim 1, further comprising means for allowing the origin and integrity of the review document to be verified, including:
   means for producing a review document record including the review document;
   means for producing a digital fingerprint for the review document by hashing the review document record using a one-way hashing method;
   a review document private key for use in encrypting the digital fingerprint of the review document to produce a first document signature, and kept confidential from viewers of the review document; and a first document public key for use in decrypting the review document signature to produce the digital fingerprint of the first document, and made available to viewers of the review document;

means for producing a digital signature for the review document by encrypting the review fingerprint using the review document private key; and means for distributing the review document record, the review document signature, and the review document public key whereby viewers of the review document can decrypt the review document signature using the review public key, produce the review document fingerprint by hashing the review document record, and compare the decryption with the fingerprint to verify the origin and integrity of the review document.

5. The reviewer workstation of claim 4, in which:

the digital signature of the review document includes identifying information that can be used to identify the first document as the document on which the review document is based.

6. The reviewer workstation of claim 5 in which:

the identifying information depends on information contained in the first document record.

7. The reviewer workstation of claim 5 in which:

the identifying information depends on a private key used for signing the first document.

8. The reviewer workstation of claim 5 in which:

the workstation further comprises means for receiving a time stamp of the first document, the time stamp including a digital stamping time; and the identifying information depends on information included in the time stamp.

9. The reviewer workstation of claim 4, in which the workstation further comprises means for allowing verification of the existence of the review document signature at the time of the review, including:

means for providing the review document signature to an electronic notary;

means for receiving a time stamp and time stamp signature for the review document from the electronic notary, the review document time stamp including the stamping time and the review document signature, the review document time stamp signature being produced from a fingerprint of the review document time stamp using a private key of the notary, the fingerprint of the review document time stamp being produced by hashing the time stamp using a one-way hashing method; and means for distributing the time stamp and time stamp signature whereby viewers of the review document can decrypt the time stamp signature using the public key of the notary, produce the time stamp fingerprint by hashing the time stamp, and compare the decryption with the fingerprint so as to verify the origin and integrity of the time stamp and the stamping time in the time stamp.

10. The reviewer workstation of claim 1, in which the log of activities includes information indicating the time for which the first document was displayed.

11. The reviewer workstation of claim 10, in which the log of activities includes information indicating the times for which portions of the first document were displayed and the order in which the portions were displayed.

12. The reviewer workstation of claim 11, in which the reviewer uses multiple displays or multiple windows on one display and the log of activities includes information indicating the times for which portions of the first document were displayed at each respective display or window.

13. The workstation of claim 1, in which the log of activities includes information indicating the times when the reviewer was looking at the display.

14. The reviewer workstation of claim 13, in which the reviewer uses multiple displays or multiple windows on one display and the log of activities includes information indicating the times during which the reviewer looked at each respective display or window.

15. The reviewer workstation of claim 1, in which the log of activities includes information entered by the reviewer during the review.

16. The workstation of claim 1, in which the log of activities includes the configuration of software used during the review.

17. The reviewer workstation of claim 1, in which the log of activities includes the configuration of hardware used during the review.

18. The reviewer workstation of claim 1, in which the log of activities includes image manipulations used during the review, the image manipulations being selected from the group including: zooming into portions of images of the first document; slow motion of a video portion of the first document; contrast adjustment of images or video; changes in color in images or video; or other digital image enhancements.

19. An authoring workstation, comprising:

means for recording a presentation document including a log of activities of a critical procedure;

means for allowing the origin and integrity of the presentation document to be verified, including:

means for producing a presentation document record including the presentation document;

means for producing a digital fingerprint for the presentation document by hashing the presentation document record using a one-way hashing method;

a private key of the presentation;

means for producing a digital signature for the presentation document by encrypting the presentation fingerprint using the private key of the presentation;

means for distributing the presentation document record, the presentation document signature, and a public key of the presentation whereby viewers of the presentation document can decrypt the presentation document, produce the presentation document fingerprint by hashing the presentation document record, compare the decryption with the fingerprint to verify the origin and integrity of the presentation document;

means for providing the presentation document signature to an electronic notary, the electronic notary residing on a host system separate from the authoring workstation;

means for receiving a time stamp and time stamp signature for the presentation document from the electronic notary, the presentation document time stamp including the stamping time at which the time stamp was produced and the presentation document signature, the presentation document time stamp signature being produced from a fingerprint of the presentation document time stamp using a private key of the electronic notary; and means for distributing the time stamp whereby viewers of the presentation document can decrypt the time stamp signature using the public key of the electronic notary, produce the time stamp fingerprint by hashing the time stamp, and compare the decryption with the fingerprint to verify the origin and integrity of the time stamp and the stamping time in the time stamp.

20. The authoring workstation of claim 19 in which:

the critical procedure is a review of medical images; and the workstation includes means for recording information indicating the time for which the images are displayed.

21. The authoring workstation of claim 19 in which:

the critical procedure is a medical operation and the workstation includes a multitude of cameras for recording the operation from different perspectives and one or more microphones for recording the audio information during the operation.

22. The authoring workstation of claim 19 in which:

the critical procedure is an inspection of a building construction to determine compliance with specifications;

the workstation includes a mobile camera and microphone for recording what an inspector sees in the building.

23. An auditor workstation, comprising:

means for obtaining a first document record, a public key of a first document, a first document time stamp, a first document time stamp signature, a review document record, a public key of a review document of the first document, a review document time stamp, a review document time stamp signature, and a public key of an electronic notary, the electronic notary residing on a separate host system from the auditor workstation;

means for decrypting the first document time stamp signature using the public key of the first document;

means for reproducing a fingerprint of the first document using a one-way hashing method;

means for comparing the first document fingerprint with the decryption of the first document signature and verifying the origin of the first document and that the first document has not been altered since it was signed, depending on the comparison;

means for producing a fingerprint for the first document time stamp by hashing the time stamp using the one-way hashing method;

means for decrypting the first document time stamp signature using the public key of the electronic notary;

means for comparing the first document time stamp fingerprint with the decryption of the first document time stamp signature and verifying the origin of the first document time stamp and that the first document time stamp has not been altered since it was signed, depending on the comparison;

means for decrypting the review document time stamp signature using the public key of the review document;

means for reproducing a fingerprint of the review document using the one-way hashing method;

means for comparing the review document fingerprint with the decryption of the review document signature and verifying the origin of the review document and that the review document has not been altered since it was signed, depending on the comparison;

means for producing the fingerprint for the review document time stamp by hashing the time stamp using the one-way hashing method;

means for decrypting the review document time stamp signature using the public key of the electronic notary;

means for comparing the review document time stamp fingerprint with the decryption of the review document time stamp signature and verifying the origin of the review document time stamp and that the review document time stamp has not been altered since it was signed, depending on the comparison; and means for auditing the review of the first document.

24. A computer network, in which:

the network comprises authoring means, including:

means for an author to produce a first document selected from a group including: means for producing an image, means for producing a report, and means for producing a multimedia production for documenting the steps preformed during a critical procedure;

means for producing a first document record containing the first document and none or more of: the identity of the author, the identity of the authoring workstation, the time of the authoring, the time of signing, the identification of other documents on which the first document depends, a sequence number of the document, and a title of the document;

means for producing a fingerprint of the first document record using a one-way hashing method;

a private key for encrypting the fingerprint of the first document to produce a first document signature and which can not be accessed by viewers of the first document; and a public key for decrypting the first document signature and which is accessible by viewers of the first document;

means for producing a first document signature by encrypting the first document fingerprint using the private key for signing first document fingerprints;

means for storing the first document record and the first document signature;

means for providing the first document signature to an electronic notary, the electronic notary residing on a separate host system of the network;

means for obtaining a time stamp and a time stamp signature from the electronic notary for the first document, the time stamp containing the first document signature and a digital time when the time stamp was produced, the first document time stamp signature being produced by encrypting a fingerprint of the first document time stamp using a private key of the electronic notary, the fingerprint of the review document time stamp being produced by hashing the first document time stamp using a one-way hashing method;

means for storing the first document time stamp and the first document time stamp signature of the electronic notary; and means for distributing to viewers of the first document: the first document record, the public key the first document, the first document time stamp, and the first document time stamp signature;

the network further comprises reviewing means, including:

means for obtaining the first document record, the first document time stamp, the first document time stamp signature, the public key of the first document, and the public key of the electronic notary;

means for decrypting the first document signature using the public key of the first document;

means for reproducing the fingerprint of the first document using the one-way hashing method; and means for comparing the first document fingerprint with the decryption of the first document signature and verifying the origin of the first document and that the first document has not been altered since it was signed, depending on the comparison;

means for producing the fingerprint for the first document time stamp by hashing the time stamp using the one-way hashing method;

means for decrypting the first document time stamp signature using the public key of the electronic notary; and means for comparing the first document time stamp fingerprint with the decryption of the first document time stamp signature and verifying the origin of the first document time stamp and that the first document time stamp has not been altered since it was signed, depending on the comparison;

means for automatically creating a review document while a human reviewer reviews the first document, the review document including a record log of the activities of the reviewer during the review, the means for creating the review document including one or more of: means for recording information indicating the periods of time for which a portion of the first document was displayed, means for recording information indicating the order in which multiple portions of the first document were displayed, means for recording information indicating the periods of time when the reviewer was looking at each of multiple respective windows or displays, means for recording information indicating the order in which the reviewer looked at respective windows or displays, means for recording information entered by the reviewer, configuration of the software of a review workstation, means for recording configuration of the hardware of a review workstation, means for recording information indicating image manipulations performed during the review;

means for producing a review document record containing the review document and information for identifying the first document on which the review document is based, selected from information depending on: information in the first document record; information in the first document time stamp; and information in both the first document record and the first document time stamp, the review document record further containing none or more of: the identity of the reviewer, the identity of the reviewer workstation, the time of the review, a sequence number for the review, and a title for the review;

means for producing a fingerprint of the review document record using a one-way hashing method;

a private key for encrypting the fingerprints of review documents to produce a review signatures and which can not be accessed by viewers of the review document; and a public key for decrypting review signatures and which is accessible by viewers of the review document;

means for producing a review document signature by encrypting the review document fingerprint using the private key for decrypting review signatures;

means for storing the review document record and the review document signature;

means for providing the review document signature to the electronic notary;

means for obtaining a time stamp and a time stamp signature from the electronic notary for the review document, the time stamp containing the review document signature and a digital time when the time stamp was produced, the review document time stamp signature being produced by the electronic notary by encrypting a fingerprint of the review document time stamp using a securely held private key of the electronic notary, the fingerprint of the review document time stamp being produced by hashing the review document time stamp using a one-way hashing method;

means for storing the review document time stamp and the review document time stamp signature of the electronic notary; and means for distributing to viewers of the review document: the review document record, the public key of the review signatures, the review document time stamp, and the review document time stamp signature;

the network further comprises auditing means including:

means for obtaining the first document record, the public key of the first document, the first document time stamp, the first document time stamp signature, the review document record, the public key of the review signature, the review document time stamp, the review document time stamp signature, and the public key of the electronic notary;

means for decrypting the first document signature using the public key of the first document;

means for reproducing the fingerprint of the first document using the one-way hashing method;

means for comparing the first document fingerprint with the decryption of the first document signature and verifying the origin of the first document and that the first document has not been altered since it was signed, depending on the comparison;

means for producing the fingerprint for the first document time stamp by hashing the time stamp using the one-way hashing method;

means for decrypting the first document time stamp signature using the public key of the electronic notary;

means for comparing the first document time stamp fingerprint with the decryption of the first document time stamp signature and verifying the origin of the first document time stamp and that the first document time stamp has not been altered since it was signed, depending on the comparison;

means for decrypting the review document signature using the public key;

means for reproducing the fingerprint of the review document using the one-way hashing method;

means for comparing the review document fingerprint with the decryption of the review document signature and verifying the origin of the review document and that the review document has not been altered since it was signed, depending on the comparison;

means for producing the fingerprint for the review document time stamp by hashing the time stamp using the one-way hashing method;

means for decrypting the review document time stamp signature using the public key of the electronic notary;

means for comparing the review document time stamp fingerprint with the decryption of the review document time stamp signature and verifying the origin of the review document time stamp and that the review document time stamp has not been altered since it was signed, depending on the comparison; and means for auditing the review of the first document;

the network further comprises electronic notarizing means, including:
  means for obtaining a document signature from a customer;
  means for determining a stamping time;
  means for producing a time stamp containing the document signature and the stamping time and none or more of: the identity of the customer; a sequence number of the time stamp; and the identity of the electronic notary;
  means for producing a fingerprint of the time stamp by hashing the time stamp using a one-way hashing method;
  a private key of the electronic notary for encrypting information and which can not be accessed by viewers of the information; and a public key of the electronic notary for decrypting information that was encrypted using the private Key and which is accessible by viewers of the information;
  means for producing a time stamp signature by encrypting the time stamp fingerprint using the private key of the electronic notary;
  means for storing the time stamp and the time stamp signature;
  means for providing the time stamp and time stamp signature to the customer; and
  means for distributing the public key to viewers of the information.

25. A secure server, comprising:
means for receiving through a secure channel, a first document from an author;
means for producing a first document record including the first document;
means for storing the first document record;
means for providing a digital signature for the first document, the signature being formed by encrypting the first document fingerprint using a first document private key;
a first document public key for viewers of the first document to use for decrypting the signature of the first document for reproducing the first document fingerprint;
means for distributing the first document record, the first document signature, and the first document public key whereby viewers of the first document can decrypt the first document signature using the public key, produce the first document fingerprint by hashing the time stamp, and compare the decryption with the fingerprint to verify the origin and integrity of the first document;
means for providing a time stamp and time stamp signature of an electronic notary for the first document, the electronic notary being on a host system different from the secure server;
means for distributing the time stamp and the time stamp signature for the first document, whereby viewers of the first document can decrypt the time stamp signature using a public key of the electronic notary, produce the time stamp fingerprint by hashing the time stamp, and compare the decryption with the fingerprint to verify the origin and integrity of the time stamp and the stamping time in the time stamp for the first document;
means for receiving through a secure channel, a review document;
means for producing a review document record, the review document record including the review document and a log of the activities of a reviewer of the first document during a review of the first document;
means for providing a digital signature for the review document, the signature being formed by encrypting the review document fingerprint using a review document private key, the signature including information for determining whether the review document is based on the first digital document;
a review document public key for viewers of the review document to use for decrypting the signature of the review document for reproducing the review document fingerprint;
means for distributing the review document record, the review document signature, and the review document public key whereby viewers of the review document can decrypt the review document signature using the review document public key, produce the review document fingerprint by hashing the review document record, and compare the decryption with the fingerprint to verify the origin and integrity of the review document and that the review document is based on the first document;
means for providing a time stamp and time stamp signature of the electronic notary for the review document;
means for distributing the time stamp and time stamp signature of the review document, whereby viewers of the review document can decrypt the time stamp signature using the public key of the electronic notary, produce the time stamp fingerprint by hashing the time stamp, and compare the decryption with the fingerprint to verify the origin and integrity of the time stamp and the stamping time in the time stamp of the review document.

26. The secure server of claim 25, in which:
the server further comprises: means for producing a digital fingerprint for the first document by hashing the first document record using a one-way hashing method; and means for producing a digital fingerprint for the review document by hashing the review document record using the one-way hashing method;
the server further comprises one or more private keys kept confidential in the server for signing first documents and review documents by encrypting respective fingerprints for the documents;
the means for providing a first document signature includes one or more of: means for encrypting the first document fingerprint using one of the private keys for the first document, and means for receiving a first document signature from the author;
the means for providing a review document signature includes one or more of: means for encrypting the review document fingerprint using one of the private keys for the review document; and means for receiving a first document signature from the reviewer;
the means for providing a time stamp and time stamp signature of a notary for the first document, includes one or more of: means for receiving the time stamp and time stamp signature for the first document from the author; and the combination of: means for providing the first document signature to an electronic notary; and means for receiving a first document time stamp and first document time stamp signature from the electronic notary, the first document time stamp including the stamping time at which the time stamp was produced and the first document signature, the first document time stamp signature being produced from a fingerprint of the first document time stamp using a private key of the notary;

the means for providing a time stamp and time stamp signature of a notary for the review document, includes one or more of: means for receiving the time stamp and time stamp signature for the first document from the reviewer; and the combination of: means for providing the review document signature to an electronic notary; and means for receiving a time stamp and time stamp signature for the review document from the electronic notary, the review document time stamp including the stamping time at which the time stamp was produced and the review document signature, the review document time stamp signature being produced from a fingerprint of the review document time stamp using a private key of the notary, the fingerprint of the review document time stamp being produced by hashing the time stamp using a one-way hashing method.

* * * * *